US012324441B2

(12) United States Patent
Iyer et al.

(10) Patent No.: US 12,324,441 B2
(45) Date of Patent: *Jun. 10, 2025

(54) HYPERIMMUNIZED EGG PRODUCT FOR TREATMENT OR PREVENTION OF CORONAVIRUS INFECTION

(71) Applicant: LAY SCIENCES, INC., Jupiter, FL (US)

(72) Inventors: Subramanian V. Iyer, Royal Palm Beach, FL (US); Satishchandran Chandrasekhar, Jupiter, FL (US); Uday Saxena, Bengaluru (IN); Gopi Kadiyala, Karnataka (IN)

(73) Assignee: Lay Sciences, Inc., Jupiter, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/308,934

(22) Filed: Apr. 28, 2023

(65) Prior Publication Data
US 2023/0285547 A1  Sep. 14, 2023

Related U.S. Application Data

(63) Continuation of application No. 17/693,280, filed on Mar. 11, 2022, now Pat. No. 11,701,423.

(60) Provisional application No. 63/160,155, filed on Mar. 12, 2021.

(51) Int. Cl.
| | |
|---|---|
| *A61K 39/215* | (2006.01) |
| *A23B 5/00* | (2006.01) |
| *A23B 5/03* | (2006.01) |
| *C07K 16/10* | (2006.01) |
| *A61K 39/00* | (2006.01) |

(52) U.S. Cl.
CPC ............. *A23B 5/03* (2013.01); *A23B 5/00* (2013.01); *A61K 39/215* (2013.01); *C07K 16/1002* (2023.08); *C07K 16/1003* (2023.08); *A61K 2039/552* (2013.01)

(58) Field of Classification Search
None
See application file for complete search history.

(56) References Cited

U.S. PATENT DOCUMENTS

| | | | |
|---|---|---|---|
| 4,748,018 A | 5/1988 | Stolle et al. | |
| 5,367,054 A | 11/1994 | Lee | |
| 5,772,999 A | 6/1998 | Greenblatt et al. | |
| 6,803,035 B2 | 10/2004 | Greenblatt et al. | |
| 7,105,158 B1 | 9/2006 | D'Souza et al. | |
| 10,434,116 B2 | 10/2019 | Frieman et al. | |
| 11,701,423 B2* | 7/2023 | Iyer .................. | C07K 16/1002 424/186.1 |
| 2004/0156857 A1 | 8/2004 | Adalsteinsson et al. | |
| 2021/0347858 A1 | 11/2021 | Starzl | |

OTHER PUBLICATIONS

CDC's Interim Clinical Considerations, Jul. 20, 2022, from https://www.cdc.gov/vaccines/covid-19/clinical-considerations/interim-considerations-us.html, accessed Aug. 9, 2022, 30 page printout (2022).
Elzoghby et al., "Albumin-based nanoparticles as potential controlled release drug delivery systems," Journal of Controlled Release, 157:168-182 (2012).
Fertel et al., "Formation of Antibodies to Prostaglandins in the Yolk of Chicken Eggs," Biochemical and Biophysical Research Communications, 102: 1028-1033 (1981).
Gallaher et al., "Analysis of Wuhan Coronavirus: Deja Vu," Virological.org 63, (2020), 88 pages.
Gallaher et al., "Analysis of Wuhan Coronavirus: Deja Vu Update Feb. 7, 2020," Virological.org 63, (2020), 97 pages.
Jensenius et al., "Eggs: Conveniently Packaged Antibodies. Methods for Purification of Yolk IgG," Journal of Immunological Methods, 46: 63-68 (1981).
Lebacq-Verheyden et al., "Quantification and Distribution of Chicken Immunoglobulins IgA, IgM and IgG in Serum and Secretions," Immunology, 27: 683-692 (1974).
Leslie et al., "Phylogeny of Immunoglobulin Structure and Function: III. Immunoglobulins of the Chicken," Journal of Experimental Medicine, 130: 1337-1352 (1969).
Tse et al., "A Novel Activiation Mechanism of Avian Influenza Virus H9N2 by Furin," Journal of Virology, 88:1673-1683 (2014).
Mathiowitz et al., "Microencapsulation," in Encyclopedia of Controlled Drug Delivery, vol. 2, pp. 495-546, 1999, John Wiley & Sons, Inc. New York, N.Y.

(Continued)

*Primary Examiner* — Stacy B Chen
(74) *Attorney, Agent, or Firm* — Dentons US LLP

(57) ABSTRACT

In one aspect, the present disclosure is directed to a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus. The present disclosure is also directed to hyperimmunized eggs and egg products produced by an animal that has been hyperimmunized with an antigen selected from i) a spike (S) protein, an S1 subunit protein, an S2 subunit protein, a receptor binding domain (RBD), and an immunogenic fragment thereof; ii) a nucleocapsid (N) protein, and an immunogenic fragment thereof; iii) a human ACE2 receptor protein, and an immunogenic fragment thereof; and iv) a human coronavirus selected from the group consisting of SARS-CoV, MERS-CoV, SARS-CoV-2, HCoV-HKU1, HCoV-NL63, HCoV-OC43 and HCoV-229E. Methods of preparing the hyperimmunized eggs and egg products are also disclosed.

14 Claims, 7 Drawing Sheets

Specification includes a Sequence Listing.

(56) References Cited

OTHER PUBLICATIONS

Matsuyama et al., "Middle East Respiratory Syndrome Coronavirus Spike Protein Is Not Activated Directly by Cellular Furin During Viral Entry into Target Cells," Journal of Virology, vol. 92, Issue 19, 2018 (e00683-18), 12 pages.
Polson et al., "Antibodies to Proteins From Yolk of Immunized Hens," Immunological Communications, 9: 495-514 (1980).
Wan et al., "Receptor Recognition by the Novel Coronavirus from Wuhan: an Analysis based on Decade-Long Structural Studies of SARS Coronavirus," Journal of Virology, vol. 94, Issue 7, 2020 (e00127-20), 9 pages.
Wrapp et al., "Cryo-EM structure of the 2019-nCoV spike in the prefusion conformation," Science, 367: 1260-1263 (2020).
Bonnin et al., "HCov-229E spike protein fusion activation by trypsin-like serine proteases is mediated by proteolytic processing in the S2' region," Journal of General Virology, 99:908-912 (2018).
Carlander et al., "Chicken Antibodies: A Clinical Chemistry Perspective," Upsala Journal of Medical Sciences, 104 (3): 179-189 (1999).
De Haan et al., "Cleavage of Group 1 Coronavirus Spike Proteins: How Furin Cleavage Is Traded Off against Heparan Sulfate Binding upon Cell Culture Adaptation," Journal of Virology, 82(12):6078-6083 (2008).
Gralinski et al., "Return of the Coronavirus: 2019-nCoV," Viruses, 12:135 (2020), doi:10.3390/v12020135, 8 pages.
Hoffmann et al., "SARS-CoV-2 Cell Entry Depends on ACE2 and TMPRSS2 and Is Blocked by a Clinically Proven Protease Inhibitor," Cell, 181:271-280.e1-e5 (2020).
Jia et al., "ACE2 Receptor Expression and Severe Acute Respiratory Syndrome Coronavirus Infection Depend on Differentiation of Human Airway Epithelia," Journal of Virology, 79(23):14614-14621 (2005).
Lin et al., "Identification of residues in the receptor-binding domain (RBD) of the spike protein of human coronavirus NL63 that are critical for the RBD-ACE2 receptor interaction," Journal of General Virology, 89:1015-1024 (2008).
Lucchese, "Epitopes for a 2019-nCoV vaccine," Cellular & Molecular Immunology, 17:539-540 (2020).
Meulenaer et al., "Isolation and Purification of Chicken Egg yolk Immunoglobulins: A Review," Food and Agricultral Immunology, 13:275-288 (2001).
Millet et al., "Host cell entry of Middle East respiratory syndrome coronavirus after two-step, furin-mediated activation of the spike protein," Proceedings of the National Academy of Sciences of the U.S.A., 111(42): 15214-15219 (2014).
Yang et al., "A novel and convenient method to immunize animals: inclusion bodies from recombinant bacteria as antigen to directly immunize animals," African Journal Biotechnology, 10(41):8146-8150 (2011).
Andersen et al., "The proximal origin of SARS-CoV-2," Nature Medicine, 26: 450-452 (2020).
GenBank Accession No. MN908947.3, "Severe acute respiratory syndrome coronavirus 2 isolate Wuhan-Hu-1, complete genome," Published: Mar. 18, 2020, 10 pages.
Saxena et al., "In silico and in vitro Demonstration of Homoharrintonine's Antagonism of RBD-ACE2 Binding and its Anti-inflammatory and anti-thrombogenic Properties in a 3D human vascular lung model," bioRxiv 2021.05.02.442384; doi: https://doi.org/10.1101/2021.05.02.442384, May 3, 2021, 18 pages.

* cited by examiner

Neutralization of SARS CoV-2 Virus - Wuhan Strain

Remdesivir Positive Control:
- % Cytotoxicity
- % Inhibition
- IC-50 ≈ 0.94 µM

ImmunIgY:
- IC$_{50}$ = 8.67 µg/mL (USA-WA1/2020 (Wuhan))
- 48.17 pM

| ug IgY | uM | nM | pM |
|---|---|---|---|
| 180,000.00 | 1 | 1,000 | 1,000,000 |
| 180.00 | 0 | 1 | 1,000 |
| 1.80 | 0.00 | 0.01 | 10.00 |
| 8.67 | 0.00 | 0.05 | 48.17 |

FIG. 6

HYPERIMMUNIZED EGG PRODUCT FOR TREATMENT OR PREVENTION OF CORONAVIRUS INFECTION

RELATED APPLICATIONS

This application is a continuation of, U.S. patent application Ser. No. 17/693,280, filed Mar. 11, 2022, which claims priority to U.S. Provisional Patent Application No. 63/160,155 filed on Mar. 12, 2021, the contents of each of which are incorporated herein in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 15809533_000003_US21_Sequence_Listing.xml. The size of the text file is 31 kilobytes, and the text file was created on Apr. 26, 2023.

BACKGROUND

Severe Acute Respiratory Syndrome coronavirus 2 (SARS-CoV-2) is the seventh member of the Coronaviridae family known to infect humans. Three of these viruses, SARS-CoV-1, MERS, and SARS-CoV-2, can cause severe disease. The remaining four, HCoV-HKU1, HCoV-NL63, HCoV-OC43 and HCoV-229E, are associated with mild respiratory symptoms. Genomic comparison of both alpha- and betacoronaviruses identifies two important features of the SARS-CoV-2 genome that distinguishes it from other members of the Coronaviridae family. First, based on structural modelling and early biochemical experiments, SARS-CoV-2 appears to be optimized for binding to the human angiotensin converting enzyme 2 (ACE2) receptor. Second, the highly variable spike (S) protein of SARS-CoV-2 has a polybasic (furin) cleavage site at the S1 and S2 boundary via the insertion of twelve nucleotides. Cleavage of coronavirus S proteins has been shown to enable cell entry. A need exists for improved methods of treating and preventing coronavirus infection in general, and SARS-CoV-2 infection in particular.

SUMMARY OF THE INVENTION

In certain aspects, the disclosure relates to a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus. In certain embodiments, the coronavirus is a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E).

In certain embodiments, the subject is infected with Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) or human coronavirus 229E (HCoV-229E. In certain embodiments, the subject has Severe Acute Respiratory Syndrome (SARS), Middle East Respiratory Syndrome (MERS) or Coronavirus Disease-2019 (COVID-19). In certain embodiments, the coronavirus is SARS-CoV-2. In certain embodiments, the subject is infected with SARS-CoV-2. In certain embodiments, the subject has Coronavirus Disease-2019 (COVID-19).

In certain embodiments, the methods disclosed herein further comprise hyperimmunizing the egg-producing animal with a composition comprising an antigen selected from the group consisting of: i) a human coronavirus spike (S) protein, a human coronavirus S1 subunit protein, a human coronavirus S2 subunit protein, and an immunogenic fragment thereof; ii) a human coronavirus nucleocapsid (N) protein, and an immunogenic fragment thereof; iii) a human ACE2 receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E.

In certain embodiments, the composition further comprises an adjuvant. In certain embodiments, the adjuvant is selected from the group consisting of Freund' complete adjuvant, Freund' incomplete adjuvant and QS21. In certain embodiments, the composition is administered to the egg-producing animal by subcutaneous injection or intramuscular injection. In certain embodiments, the composition is administered to the egg-producing animal at least twice and at an interval from once every 2 weeks to once every 3 months. In certain embodiments, the one or more antibodies to the human coronavirus in the hyperimmunized egg product have a titer of at least 200,000 as measured by optical density. In certain embodiments, the titer of at least 200,000 is maintained in hyperimmunized egg products produced by the egg-producing animal for at least two weeks. In certain embodiments, the hyperimmunized egg product is administered to the subject as an oral rinse, by inhalation, by nasal drops, or by eye drops. In certain embodiments, the hyperimmunized egg product is a whole egg, an egg yolk, or purified or partially purified IgY. In certain embodiments, the hyperimmunized egg product is a liquid, a freeze-dried powder, or formulated to be administered as a spray. In certain embodiments, the hyperimmunized egg product is formulated to contain GRAS components and excipients to improve solubility, stability and dissolution.

In certain embodiments, the methods disclosed herein further comprise collecting a hyperimmunized egg from the egg-producing animal that has been hyperimmunized, and preparing a hyperimmunized egg product from the hyperimmunized egg. In certain embodiments, the hyperimmunized egg product comprises at least 20% more by weight of an IgY antibody specific to the coronavirus relative to a control egg product obtained from an egg-producing animal that is not hyperimmunized. In certain embodiments, the subject is a human. In certain embodiments, the coronavirus is a coronavirus that infects humans.

In certain aspects, the disclosure relates to a hyperimmunized egg produced by an animal that has been hyperimmunized with an antigen selected from the group consisting of: i) a human coronavirus spike (S) protein, a human coronavirus S1 subunit protein, a human coronavirus S2 subunit protein, and an immunogenic fragment thereof; ii) a human coronavirus nucleocapsid (N) protein, and an immunogenic fragment thereof; iii) a human angiotensin converting enzyme 2 (ACE2) receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E, wherein the level of antibodies to the antigen in the hyperimmunized egg is increased relative to an egg from an animal that has not been hyperimmunized. In certain embodiments, the antibodies in the hyperimmunized egg have a titer of at least one million as measured by optical density. In certain aspects, the disclosure relates to a hyperimmunized egg product obtained from a hyperimmunized egg described herein. In certain embodiments, the hyperimmunized egg product is whole egg, egg yolk, or purified or partially purified IgY antibody to the coronavirus.

In certain aspects, the disclosure relates to a pharmaceutical composition comprising a hyperimmunized egg product as disclosed herein and a pharmaceutically acceptable carrier. In certain embodiments, the pharmaceutical composition is formulated for oral, nasal or ocular administration. In certain embodiments, the pharmaceutical composition is formulated for administration to the subject as an oral rinse, by inhalation, by nasal drops or by eye drops. In certain embodiments, the pharmaceutical composition is a liquid, a freeze-dried powder, or formulated to be administered as a spray. In certain embodiments, the pharmaceutically acceptable carrier comprises a compound that is generally recognized as safe (GRAS) and an excipient that improves solubility, stability and/or dissolution. In certain embodiments, the hyperimmunized egg product is formulated in nanoparticles or in an emulsion.

In certain aspects, the disclosure relates to a method of preparing a hyperimmunized egg product comprising: a) hyperimmunizing an egg-producing animal with a composition comprising an antigen selected from the group consisting of: i) a human coronavirus spike (S) protein, a human coronavirus S1 subunit protein, a human coronavirus S2 subunit protein, and an immunogenic fragment thereof; ii) a human coronavirus nucleocapsid (N) protein, and an immunogenic fragment thereof; iii) a human Angiotensin converting enzyme 2 (ACE2) receptor protein, and an immunogenic fragment thereof; and iv) a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E); and b) preparing a hyperimmunized egg product from one or more eggs produced by the animal.

In certain embodiments, the composition further comprises an adjuvant. In certain embodiments, the adjuvant is selected from the group consisting of Freund' complete adjuvant, Freund' incomplete adjuvant and QS21. In certain embodiments, the composition is administered to the egg-producing animal by subcutaneous injection or intramuscular injection. In certain embodiments, the composition is administered to the egg-producing animal at least twice and at an interval from once every 2 weeks to once every 3 months. In certain embodiments, the egg-producing animal is a chicken. In certain embodiments, the human coronavirus is SARS-CoV-2.

Provided is a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus. The coronavirus can be a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E).

The method can minimize risk of infection in a subject. The method can treat a subject that is infected with Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) or human coronavirus 229E (HCoV-229E. The method can treat a subject that has Severe Acute Respiratory Syndrome (SARS), Middle East Respiratory Syndrome (MERS) or Coronavirus Disease-2019 (COVID-19).

In some applications, the method can prevent or treat a subject where the coronavirus is SARS-CoV-2. The method can treat a subject infected with SARS-CoV-2. The method can treat a subject that has Coronavirus Disease-2019 (COVID-19).

The method can include hyperimmunizing the egg-producing animal with a composition comprising an antigen. The composition can include one or a combination of antigens. The antigen can be selected from the group consisting of: i) a human coronavirus spike (S) protein, a human coronavirus S1 subunit protein, a human coronavirus S2 subunit protein, a human coronavirus receptor binding domain (RBD), and an immunogenic fragment thereof; ii) a human coronavirus nucleocapsid (N) protein, and an immunogenic fragment thereof; iii) a human ACE2 receptor protein, and an immunogenic fragment thereof; iv) a human coronavirus selected from the group consisting of SARS CoV-1, MERS, SARS-CoV-2, HCoV-HKU1, HCoV-NL63, HCoV-OC43 and HCoV-229E; v) a human coronavirus S protein, or an immunogenic fragment thereof; vi) an S protein of SARS-CoV-2, or an immunogenic fragment thereof; vii) a receptor binding domain (RBD) of a human coronavirus S protein, or an immunogenic fragment thereof; viii) a receptor binding domain (RBD) of SARS-CoV-2, or an immunogenic fragment thereof; ix) the amino acid sequence of SEQ ID NO: 16, or an immunogenic fragment thereof; and x) the amino acid sequence of SEQ ID NO: 19, or an immunogenic fragment thereof;

In the methods provided herein, the composition for hyperimmunizing the egg-producing animal can include an adjuvant. In some methods, the adjuvant is selected from the group consisting of Freund's complete adjuvant, Freund's incomplete adjuvant and QS21. In some methods, the adjuvant is selected from the group consisting of Freund's complete adjuvant, Freund's incomplete adjuvant, a saponin, a biodegradable polymer, aluminum hydroxide, mineral oil, a surfactant, and combinations thereof. The composition can be administered to the egg-producing animal by subcutaneous injection or intramuscular injection. The composition can be administered to the egg-producing animal at least twice and at an interval from once every 2 weeks to once every 3 months.

In the methods provided herein, the egg produced by the hyperimmunized animal can include one or more antibodies to the human coronavirus. A product produced from the egg (a hyperimmunized egg product) can be a whole egg, an egg yolk, or purified or partially purified IgY. The hyperimmunized egg product can have a titer of at least 80,000 as measured by optical density. The titer of at least 80,000 can be maintained in the hyperimmunized egg product produced by the egg-producing animal for at least two weeks.

In the methods provided herein, the hyperimmunized egg product can be administered to the subject via any delivery mechanism known in the art. The hyperimmunized egg product can be administered to the subject as an oral rinse, by inhalation, by nasal drops, or by eye drops. The hyperimmunized egg product can be a liquid, a freeze-dried powder, or formulated to be administered as a spray. The hyperimmunized egg product can be a beverage. The hyperimmunized egg product can be formulated to contain GRAS components, or excipients to improve solubility, stability and dissolution, or both.

The method provided herein cam further include collecting a hyperimmunized egg from the egg-producing animal that has been hyperimmunized, and preparing a hyperimmunized egg product from the hyperimmunized egg. The hyperimmunized egg product from one or more eggs produced by the animal can be prepared by dehydrating, spray drying, or freeze drying of whole egg, yolk, or a purified IgY fraction from the one or more eggs. The hyperimmunized egg product can be formulated or prepare as nanoparticles or an emulsion. The emulsion can be a microemulsion or a nanoemulsion. The hyperimmunized egg product can be microencapsulated. The hyperimmunized egg product can include at least 20% more by weight of an IgY antibody specific to the coronavirus relative to a control egg product obtained from an egg-producing animal that is not hyperimmunized.

In the methods provided herein, the subject can be a human. In such methods, the coronavirus is a coronavirus that infects humans.

In the methods, administration of the hyperimmunized egg product to the subject can reduce binding of the coronavirus to an angiotensin converting enzyme 2 (ACE2) receptor protein in the subject. Administration of the hyperimmunized egg product to the subject can reduce entry of the coronavirus into a cell of the subject.

Administration of the hyperimmunized egg product to the subject can reduce binding of the coronavirus to an angiotensin converting enzyme 2 (ACE2) receptor protein in the subject and reduce entry of the coronavirus into a cell of the subject.

Also provided is one or more than one hyperimmunized egg produced by an animal that has been hyperimmunized with an antigen selected from the group consisting of i) a human coronavirus spike (S) protein, a human coronavirus S1 subunit protein, a human coronavirus S2 subunit protein, a human coronavirus receptor binding domain (RBD), and an immunogenic fragment thereof; ii) a human coronavirus nucleocapsid (N) protein, and an immunogenic fragment thereof; iii) a human angiotensin converting enzyme 2 (ACE2) receptor protein, and an immunogenic fragment thereof; iv) a human coronavirus selected from the group consisting of SARS CoV-1, MERS, SARS-CoV-2, HCoV-HKU1, HCoV-NL63, HCoV-OC43 and HCoV-229E; v) a human coronavirus S protein, or an immunogenic fragment thereof; vi) an S protein of SARS-CoV-2, or an immunogenic fragment thereof; vii) a receptor binding domain (RBD) of a human coronavirus S protein, or an immunogenic fragment thereof; viii) a receptor binding domain (RBD) of SARS-CoV-2, or an immunogenic fragment thereof; ix) the amino acid sequence of SEQ ID NO: 16, or an immunogenic fragment thereof; and x) the amino acid sequence of SEQ ID NO: 19, or an immunogenic fragment thereof. The level of antibodies to the antigen in the hyperimmunized egg is increased relative to an egg from an animal that has not been hyperimmunized. The antibodies in the hyperimmunized egg have a titer of at least 80,000 as measured by optical density.

Also provided is a hyperimmunized egg product obtained from the hyperimmunized egg produced by the methods provided herein. The hyperimmunized egg product can be whole egg, egg yolk, or purified or partially purified IgY antibody to the coronavirus. The hyperimmunized egg product can be dehydrated, spray dried or freeze dried. The hyperimmunized egg product can be formulated in nanoparticles or in an emulsion.

Also provided is a pharmaceutical composition comprising the hyperimmunized egg product provided herein and a pharmaceutically acceptable carrier. The pharmaceutically acceptable carrier can include a compound that is generally recognized as safe (GRAS), or can include an excipient that improves solubility, stability and/or dissolution, or can include both a compound that is generally recognized as safe (GRAS), or can include an excipient that improves solubility, stability and/or dissolution. The pharmaceutical composition can be formulated for oral, nasal or ocular administration. The pharmaceutical composition can be formulated for administration to the subject as an oral rinse, by inhalation, by nasal drops or by eye drops. The pharmaceutical composition can be a liquid, a freeze-dried powder, or formulated to be administered as a spray.

Also provided are methods of preparing a hyperimmunized egg product. The methods include a) hyperimmunizing an egg-producing animal with a composition comprising an antigen of a coronavirus; and b) preparing a hyperimmunized egg product from one or more eggs produced by the animal by dehydrating, spray drying, or freeze drying of whole egg, yolk or a purified IgY fraction from the one or more eggs. The antigen can include a human coronavirus spike (S) protein, a human coronavirus S1 subunit protein, a human coronavirus S2 subunit protein, a human coronavirus receptor binding domain (RBD), and an immunogenic fragment thereof. The antigen can include a human coronavirus nucleocapsid (N) protein, and an immunogenic fragment thereof. The antigen can include a human Angiotensin converting enzyme 2 (ACE2) receptor protein, and an immunogenic fragment thereof. The antigen can include a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E). The antigen can include a human coronavirus S protein, or an immunogenic fragment thereof. The antigen can include an S protein of SARS-CoV-2, or an immunogenic fragment thereof. The antigen can include a receptor binding domain (RBD) of a human coronavirus S protein, or an immunogenic fragment thereof. The antigen can include a receptor binding domain (RBD) of SARS-CoV-2, or an immunogenic fragment thereof. The antigen can include the amino acid sequence of SEQ ID NO: 16, or an immunogenic fragment thereof. The antigen can include the amino acid sequence of SEQ ID NO: 19, or an immunogenic fragment thereof. The antigen can be the amino acid sequence of SEQ ID NO: 19, or an immunogenic fragment thereof. The composition for hyperimmunizing the egg-producing animal can include two or more of the antigens mentioned in this paragraph.

BRIEF DESCRIPTION OF THE DRAWINGS

FIG. 6 shows the neutralizing activity of an oral rinse of an anti-RBD IgY antibody containing drink in an unvaccinated volunteer.

DETAILED DESCRIPTION AND PREFERRED EMBODIMENTS

Figure 1:
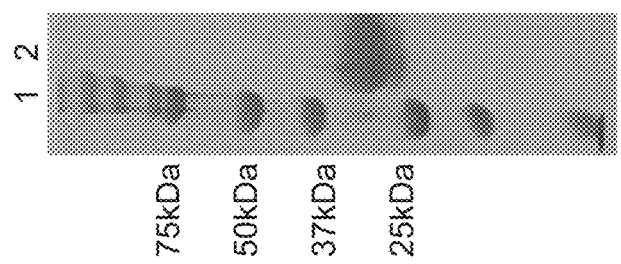
FIG. 1 shows SDS-PAGE analysis of CHO cell expressed recombinant RBD peptide. Lane 1: Molecular Weight Ladder, Lane 2: RBD.

The term "hyperimmunization" means repeated exposure to one or more antigens such that an immune response is elevated and maintained above the natural unexposed state.

A "hyperimmune state" refers to an elevated immune response in an egg producing animal that has been hyperimmunized.

The term "egg" as used herein refers to a whole egg (table, hyperimmunized or otherwise). The term "egg product" as used herein refers to a whole egg or any product or fraction obtained from a whole egg. In a particular embodiment, the egg product is an egg yolk, for example, an egg yolk powder. In another embodiment, the egg product is an egg white, for example, an egg white powder. In another embodiment, the egg product is obtained from a whole egg, for example, a whole egg powder (e.g. a spray-dried whole egg powder).

The term "control egg" refers to an egg obtained from an egg-producing animal that is not maintained in a hyperimmunized state, i.e. an animal that has not been hyperimmunized. The term "control egg product" refers to a control egg or an egg product obtained from a control egg.

The term "hyperimmunized egg" refers to a whole egg obtained from an egg-producing animal maintained in a hyperimmune state, i.e. an egg-producing animal that has been hyperimmunized. The term "hyperimmunized egg product" refers to a hyperimmunized egg or any product obtained from a hyperimmunized egg.

In certain embodiments, the hyperimmunized egg product is a concentrate. As used herein the term "concentrate" refers to a hyperimmunized egg product that is at least partially purified, such that the concentration of antibodies in the concentrate is greater than the concentration of antibodies in a hyperimmunized egg.

The term "egg powder" refers to a whole egg that has been dried. In some embodiments, the egg powder is spray-dried.

The term "egg-producing animal" means any oviparous animal, and includes any animal that lays an egg, such as avians, fish and reptiles.

The term "avian" refers to an animal that is a member of the class Ayes. Avians include, but are not limited to, chickens, turkeys, geese, ducks, pheasants, quail, pigeons and ostriches.

The term "supranormal levels" means levels in excess of those found in eggs of egg-producing animals that are not hyperimmunized. For example, supranormal levels of an antibody to a particular antigen are levels of the antibody in excess of those found in eggs of egg-producing animals that are not hyperimmunized with the particular antigen.

The term "administer" means any method of providing a subject with a substance, including orally, intranasally, parenterally (intravenously, intramuscularly, or subcutaneously), rectally, topically or intraocularly.

The term "antigen" refers to a substance that is able to induce a humoral antibody and/or cell-mediated immune response rather than immunological tolerance. The term signifies the ability to stimulate an immune response as well as react with the products of it, e.g., an antibody.

As used herein, an "antibody" is a protein that includes at least one complementarity determining region that binds to a specific target antigen, e.g. antigen A, B, C, D, Co1, Co2, H, or ET-50 disclosed herein. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. In a particular embodiment, the antibody is a polyclonal antibody. The term "polyclonal antibody", as used herein, refers to a population of antibody molecules that that are capable of immunoreacting with different epitopes on a particular antigen. In a particular embodiment, the antibody is an IgY antibody.

As used herein, the term "effective amount" refers to the amount of hyperimmunized egg product which when administered to a subject is sufficient to prevent or treat coronavirus (e.g. SARS-CoV-2) infection. The effective amount can vary depending, for example, on the age, weight, and/or health of the subject to be treated.

Coronaviruses

Coronaviruses are positive-sense single-stranded RNA viruses belonging to the family Coronaviridae. These viruses mostly infect animals, including birds and mammals. In humans, they generally cause mild respiratory infections, such as those observed in the common cold. Prior to 2002, coronaviruses were not considered to be significant human pathogens. For example, human coronaviruses such as HCoV-229E and HCoV-OC43 resulted in only mild respiratory infections in healthy adults. In 2002, however, severe acute respiratory syndrome coronavirus (SARS-CoV) emerged in Guangdong Province, China. This virus rapidly spread to 29 different countries, resulting in 8,273 confirmed cases and 775 (9%) deaths. See U.S. Pat. No. 10,434,116.

Middle East respiratory syndrome coronavirus (MERS-CoV) is a more recently emerging virus. In 2012, Middle East respiratory syndrome coronavirus (MERS-CoV), was detected in a patient with severe respiratory disease in Saudi Arabia. The clinical features of MERS-CoV infection in humans range from asymptomatic to very severe pneumonia with the potential development of acute respiratory distress syndrome, septic shock, and multiorgan failure resulting in death. Dipeptidyl peptidase 4 (also known as CD26) has been identified as the functional cellular receptor for MERS-CoV. Ecological studies have suggested that the virus is of animal origin and is most closely related to coronaviruses found in a number of species of bats, with MERS-CoV viral sequences now found in camels in Saudi Arabia. See U.S. Pat. No. 10,434,116.

Severe Acute Respiratory Syndrome coronavirus 2 (SARS-CoV-2) has mostly recently emerged in 2019 as a significant human pathogen. After causing an initial cluster of Pneumonia in Wuhan City, Hubei Province, SARS-CoV-2 quickly spread through South East Asia and within a few weeks to Europe, Africa, and America. Initial estimates suggested a mortality rate of 2% and that ~18% of the cases show severe symptoms, although such estimates are still subject to changes. See Lucchese, 2020, Epitopes for a 2019-nCoV vaccine, Nature, doi.org/10.1038/s41423-020-0377-z.

Two notable features of the SARS-CoV-2 genome have been identified. First, based on structural modelling and early biochemical experiments, SARS-CoV-2 appears to be optimized for binding to the human ACE2 receptor. Second, the highly variable spike (S) protein of SARS-CoV-2 has a polybasic (furin) cleavage site at the S1 and S2 boundary via the insertion of twelve nucleotides. Additionally, this event led to the acquisition of three predicted O-linked glycans around the polybasic cleavage site. See Andersen et al., 2020, The Proximal Origin of SARS-CoV-2, Virological.org.

The receptor binding domain (RBD) in the spike protein of SARS-CoV and SARS-related coronaviruses is the most variable part of the virus genome. Six residues in the RBD appear to be critical for binding to the human ACE2 receptor and determining host range. See Wan et al., 2020, Receptor recognition by novel coronavirus from Wuhan: An analysis based on decade-long structural studies of SARS. J. Virol. (2020) doi:10.1128/JVI.00127-20. Using coordinates based on the Urbani strain of SARS-CoV, they are Y442, L472, N479, D480, T487, and Y491l. The corresponding residues in SARS-CoV-2 are L455, F486, Q493, S494, N501, and Y505. Based on modeling and biochemical experiments, SARS-CoV-2 seems to have an RBD that can bind with high affinity to ACE2 from human, non-human primate, ferret, pig, and cat, as well as other species with high receptor homology. In contrast, SARS-CoV-2 can bind less efficiently to ACE2 in other species associated with SARS-like viruses, including rodents and civets. See Wan et al., cited above.

The phenylalanine (F) at residue 486 in the SARS-CoV-2 S protein corresponds to L472 in the SARS-CoV Urbani strain. Notably, in SARS-CoV cell culture experiments the L472 mutates to phenylalanine (L472F), which is predicted to be optimal for binding of the SARS-CoV RBD to the human ACE2 receptor. While these analyses suggest that SARS-CoV-2 may be capable of binding the human ACE2 receptor with high affinity, the interaction is not predicted to be optimal. Additionally, several of the key residues in the RBD of SARS-CoV-2 are different to those previously described as optimal for human ACE2 receptor binding. In contrast to these computational predictions, recent binding studies indicate that SARS-CoV-2 binds with high affinity to human ACE2. See Wrapp et al., 2020, Cryo-EM Structure of the 2019-nCoV Spike in the Prefusion Conformation. bioRxiv 2020.02.11.944462 doi:10.1101/2020.02.11.944462. Thus, the SARS-CoV-2 spike appears to be the result of selection on human or human-like ACE2 permitting another optimal binding solution to arise.

The second notable feature of SARS-CoV-2 is a predicted polybasic cleavage site (RRAR) in the spike protein at the junction of S1 and S2, the two subunits of the spike protein. See Gallaher, 2020, Analysis of Wuhan coronavirus: deja vu. Virological.org 63. In addition to two basic arginines and an alanine at the cleavage site, a leading proline is also inserted; thus, the fully inserted sequence is PRRA. The strong turn created by the proline insertion is predicted to result in the addition of O-linked glycans to S673, T678, and S686 that flank the polybasic cleavage site. A polybasic cleavage site has not previously been observed in related lineage B betacoronaviruses and is a unique feature of SARS-CoV-2. Some human betacoronaviruses, including HCoV-HKU1 (lineage A), have polybasic cleavage sites, as well as predicted O-linked glycans near the S1/S2 cleavage site.

While the functional consequence of the polybasic cleavage site in SARS-CoV-2 is unknown, experiments with SARS-CoV have shown that engineering such a site at the S1/S2 junction enhances cell-cell fusion but does not affect virus entry. Polybasic cleavage sites allow effective cleavage by furin and other proteases, and can be acquired at the junction of the two subunits of the haemagglutinin (HA) protein of avian influenza viruses in conditions that select for rapid virus replication and transmission (e.g. highly dense chicken populations). HA serves a similar function in cell-cell fusion and viral entry as the coronavirus S protein. Acquisition of a polybasic cleavage site in HA, by either insertion or recombination, converts low pathogenicity avian influenza viruses into highly pathogenic forms. See Longping et al., 2014, J. Virol. 88: 1673-1683.

The Delta strain of SARS-CoV-2 virus previously emerged as a dominant strain. The Delta variant RBD is mutated with three amino acid changes from the native RBD. These mutations make this variant more transmissible and infective relative to the native strain.

Hyperimmunized Egg Product

In certain aspects, the present disclosure relates to a method of preparing a hyperimmunized egg product comprising: a) hyperimmunizing an egg-producing animal with a composition comprising an antigen selected from the group consisting of: i) a human coronavirus spike (S) protein, a human coronavirus S1 subunit protein, a human coronavirus S2 subunit protein, a human coronavirus receptor binding domain (RBD), and an immunogenic fragment thereof; ii) a human coronavirus nucleocapsid (N) protein, and an immunogenic fragment thereof; iii) a human ACE2 receptor protein, and an immunogenic fragment thereof; and iv) a human coronavirus selected from the group consisting of Severe Acute Respiratory Syndrome coronavirus (SARS-CoV), Middle East Respiratory Syndrome coronavirus (MERS-CoV), Severe Acute Respiratory Syndrome coronavirus 2 (SARS-CoV-2), human coronavirus HKU1 (HCoV-HKU1), human coronavirus NL63 (HCoV-NL63), human coronavirus OC43 (HCoV-OC43) and human coronavirus 229E (HCoV-229E); and b) preparing a hyperimmunized egg product from one or more eggs produced by the animal. In some embodiments, the antigen comprises or consists of a human coronavirus RBD, e.g., a SARS-CoV-2 RBD.

In certain aspects, the present disclosure relates to a hyperimmunized egg produced by an animal that has been hyperimmunized with an antigen selected from the group consisting of: i) a human coronavirus spike (S) protein, a human coronavirus S1 subunit protein, a human coronavirus S2 subunit protein, a human coronavirus receptor binding domain (RBD), and an immunogenic fragment thereof; ii) a human coronavirus nucleocapsid (N) protein, and an immunogenic fragment thereof; iii) a human ACE2 receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E, wherein the level of antibodies to the antigen in the hyperimmunized egg is increased relative to an egg from an animal that has not been hyperimmunized. In some embodiments, the antigen comprises or consists of a human coronavirus RBD, e.g., a SARS-CoV-2 RBD, or an immunogenic fragment thereof.

Egg-producing animals produce antibodies in blood and eggs that are specific to particular immunogens. For example, various genera of the class Ayes, such as chickens (Gallus domesticus), turkeys, and ducks produce antibodies against antigens associated with avian diseases. LeBacq-Verheyden et al. (Immunology 27:683 (1974)) and Leslie, G. A., et al. (J. Med. 130:1337 (1969)), have quantitatively analyzed immunoglobulins of the chicken. Polson, A., et al. (Immunological Communications 9:495-514 (1980)) immunized hens against several proteins and natural mixtures of proteins, and detected IgY antibodies in the yolks of the eggs. Fertel, R., et al. (Biochemical and Biophysical Research Communications 102:1028-1033 (1981)) immunized hens against prostaglandins and detected antibodies in the egg yolk. Jensenius et al. (Journal of Immunological Methods 46:63-68 (1981)) provide a method of isolating egg yolk IgG for use in immunodiagnostics. Polson et al. (Immunological Communications 9:475-493 (1980)) describe antibodies isolated from the yolk of hens that were immunized with a variety of plant viruses.

U.S. Pat. No. 4,748,018 discloses a method of passive immunization of a mammal that comprises parenterally administering purified antibody obtained from the eggs of an avian that has been immunized against the corresponding antigen, and wherein the mammal has acquired immunity to the eggs.

U.S. Pat. No. 5,772,999, assigned to DCV-Biologics, discloses a method of preventing, countering or reducing chronic gastrointestinal disorders or Non-Steroidal Anti-Inflammatory Drug-induced (NSAID-induced) gastrointestinal damage in a subject by administering hyperimmunized egg and/or milk or fractions thereof to the subject.

An immunized egg is an egg which comes from an avian which has been immunized with, for example, a specific antigen or mixture of antigens. A hyperimmunized egg is an egg which comes from an avian which has been brought to a specific state of immunization by means of, for example, periodic booster administrations of antigens. Hyperimmunized eggs, no matter the type of antigen their avian maker has been administered, have been found to have various beneficial factors, including, as mentioned above, the treatment of chronic gastrointestinal disorders, NSAID-induced gastrointestinal damage (see U.S. Pat. No. 5,772,999) and anti-inflammatory effects due to the presence of an anti-inflammatory composition (see U.S. Application Publication No. US 2004/0156857).

One of the advantages of the hyperimmunized egg product is that it would have a higher and more consistent level of antibodies (e.g. IgY antibodies) to one or more of the antigens described herein compared to a control egg product or an egg product from a chicken that has been immunized with the antigen using standard immunization techniques. Typically standard immunization consists of an initial immunization followed by one or two booster immunization at 30 day intervals. In some embodiments, hyperimmunization comprises at least 4, 5, 6, 7, 8, 9 or 10 immunizations with an antigen described herein. In some embodiments, hyperimmunization comprises immunizing an egg producing animal with an antigen described herein at intervals of less than 30 days, less than 25 days, less than 20 days, less than 15 days, less than 10 days, or less than 5 days. In some embodiments, hyperimmunization comprises immunizing an egg producing animal with an antigen described herein at an interval of 1 week, 2 weeks, 3 weeks, 4 weeks, 1 month, 2 months or 3 months. Any of these values can be used to define a range for the interval at which the egg producing animal is immunized. For example, in some embodiments, the egg producing animal is hyperimmunized at an interval ranging from once every 2 weeks to once every 3 months, once per week to once every 3 months, or once every 2 weeks to once per month.

The hyperimmunized egg product can be produced by any egg-producing animal. It is preferred that the animal be a member of the class Ayes or, in other words, an avian. Within the class Ayes, domesticated fowl are preferred, but other members of this class, such as turkeys, ducks, and geese, are a suitable source of hyperimmune egg product. In a particular embodiment, the egg-producing animal is a chicken.

This special state of hyperimmunization is preferably achieved by administering an initial immunization, followed by periodic boosters with sufficiently high doses of specific antigens or mixtures of antigens. The dosage of the booster can be 10%, 20%, 30%, 40%, 50%, 60%, 70%, 80%, 90% or 100% of the dosage necessary to produce primary immunization of the egg-producing animal. Any of these percentages can be used to define a range for the dosage of the booster immunization. For example, in some embodiments, the dosage of the booster is 20%-80%, 30%-70%, or 50%-100% of the dosage necessary to produce primary immunization of the egg-producing animal. In a particular embodiment, the dosage of the booster immunization is 50% of the dosage of the primary immunization.

Having knowledge of the requirement for developing and maintaining a hyperimmune state, it is within the skill of the art to vary the amount of antigen administered, depending on the egg-producing animal genera and strain employed, in order to maintain the animal in the hyperimmune state.

The hyperimmune state can be produced by a single antigen or a combination of antigens. Hyperimmunization can be achieved by multiple exposures to multiple antigens, or multiple exposures to a single antigen.

Antigens for Hyperimmunization

In some embodiments, the antigens for hyperimmunization comprise one or more of:

i) a human coronavirus spike (S) protein, a human coronavirus S1 subunit protein, a human coronavirus S2 subunit protein, a human coronavirus receptor binding domain (RBD), and an immunogenic fragment thereof;

ii) a human coronavirus nucleocapsid (N) protein, and an immunogenic fragment thereof;

iii) a human ACE2 receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E.

In some embodiments, the antigens for hyperimmunization are selected from a SARS-CoV-2 spike protein, a SARS-CoV-2 S1 subunit protein, a SARS-CoV-2 S2 subunit protein, SARS-CoV-2, and immunogenic fragments thereof.

In some embodiments, the antigen comprises or consists of a human coronavirus RBD, e.g., a SARS-CoV-2 RBD, or an immunogenic fragment thereof.

In some embodiments, an immunogenic fragment as described herein comprises at least 10, 20, 30, 40, 50, 60, 70, 80, 90, 100, 200, 300, 400 or 500 amino acid residues.

The entire amino acid sequence of SARS-CoV-2 has been published as GenBank Accession No. MN908947.3, which is incorporated by reference herein in its entirety.

Coronavirus S Proteins

The membrane of coronaviruses harbors a trimeric transmembrane spike (S) glycoprotein which is essential for entry of virus particles into the cell. The S protein contains two functional domains: a receptor binding domain, and a second domain which contains sequences that mediate fusion of the viral and cell membranes. The S glycoprotein must be cleaved by cell proteases to enable exposure of the fusion sequences and hence is needed for cell entry.

The SARS-CoV-2 spike (S) protein is a viral surface glycoprotein that mediates binding to the human ACE2 receptor and cellular entry. The spike protein is a large type I transmembrane protein containing two subunits, an N-terminal S1 subunit and a C-terminal S2 subunit. S1 mainly contains a receptor binding domain (RBD), which is responsible for recognizing the cell surface receptor. S2 contains basic elements needed for the fusion of the virus to the cell membrane. The S protein plays key parts in the induction of neutralizing-antibody and T-cell responses, as well as protective immunity. See Gralinski et al., 2020, Viruses 12.2, 135. A key feature of coronavirus S proteins is that the proteolytic cleavage events that lead to membrane fusion can occur both at the interface of the receptor binding (S1) and fusion (S2) domains (S1/S2), as well as in a novel position adjacent to a fusion peptide within S2 (S2'). See Millet et al., 2014, PNAS 111 (42): 15214-15219.

The amino acid sequence of the SARS-CoV-2 spike (S) protein is provided below (SEQ ID NO: 1). The S1/S2 cleavage site occurs between amino acid residues R685 and S686. Accordingly, the S1 domain of SARS-CoV-2 S protein is amino acid residues 1-685 of SEQ ID NO: 1, and the S2 domain of SARS-CoV-2 S protein is amino acid residues 686-1273 of SEQ ID NO: 1. The S2' cleavage site occurs between amino acid residues R815 and S816. See Hoffmann et al., 2020, Cell 181: 1-10, which is incorporated by reference herein in its entirety. The cleavage sites are shown in bold and underlined. In some embodiments, the antigen for hyperimmunization comprises or consists of the amino acid sequence of SEQ ID NO: 1, or an amino acid sequence having at least 80%, 85%, 90%, 95%, 96%, 97%, 98% or 99% sequence identity to SEQ ID NO: 1.

```
                                          (SEQ ID NO: 1)
MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF
```

```
                         -continued
VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

IGAEHVNNSYECDIPIGAGICASYQTQTNSPRRARSVASQSIIAYTMSLG

AENSVAYSNNSIAIPTNFTISVTTEILPVSMTKTSVDCTMYICGDSTECS

NLLLQYGSFCTQLNRALTGIAVEQDKNTQEVFAQVKQIYKTPPIKDFGGF

NFSQILPDPSKPSKRSFIEDLLFNKVTLADAGFIKQYGDCLGDIAARDLI

CAQKFNGLTVLPPLLTDEMIAQYTSALLAGTITSGWTFGAGAALQIPFAM

QMAYRFNGIGVTQNVLYENQKLIANQFNSAIGKIQDSLSSTASALGKLQD

VVNQNAQALNTLVKQLSSNFGAISSVLNDILSRLDKVEAEVQIDRLITGR

LQSLQTYVTQQLIRAAEIRASANLAATKMSECVLGQSKRVDFCGKGYHLM

SFPQSAPHGVVFLHVTYVPAQEKNFTTAPAICHDGKAHFPREGVFVSNGT

HWFVTQRNFYEPQIITTDNTFVSGNCDVVIGIVNNTVYDPLQPELDSFKE

ELDKYFKNHTSPDVDLGDISGINASVVNIQKEIDRLNEVAKNLNESLIDL

QELGKYEQYIKWPWYIWLGFIAGLIAIVMVTIMLCCMTSCCSCLKGCCSC

GSCCKFDEDDSEPVLKGVKLHYT
```

The SARS-CoV-2 spike protein contains a receptor binding domain (RBD) that directly binds to angiotensin receptor 2 (ACE2) present in human cells such as lung epithelium cells. The amino acid sequence of the SARS-CoV-2 RBD is underlined in the spike protein sequence above, and is provided herein as SEQ ID NO: 16. In some embodiments, the antigen for hyperimmunization comprises or consists of the amino acid sequence of SEQ ID NO: 16, or an amino acid sequence having at least 80%, 85%, 90%, 95%, 96%, 97%, 98% or 99% sequence identity to SEQ ID NO: 16.

The amino acid sequence of the SARS-CoV S protein is provided herein as SEQ ID NO: 2. The S1/S2 cleavage site occurs between amino acid residues R667 and S668. Accordingly, the S1 domain of SARS-CoV S protein is amino acid residues 1-667 of SEQ ID NO: 2, and the S2 domain of SARS-CoV S protein is amino acid residues 668-1255 of SEQ ID NO: 2. The S2' cleavage site occurs between amino acid residues R797 and S798. See Hoffmann et al., 2020, Cell 181: 1-10. In some embodiments, the antigen for hyperimmunization comprises or consists of the amino acid sequence of SEQ ID NO: 2, or an amino acid sequence having at least 80%, 85%, 90%, 95%, 96%, 97%, 98% or 99% sequence identity to SEQ ID NO: 2.

The amino acid sequence of the MERS S protein is provided herein as SEQ ID NO: 3. The S1/S2 cleavage site occurs between amino acid residues R748 and S749. Accordingly, the S1 domain of MERS S protein is amino acid residues 1-748 of SEQ ID NO: 3, and the S2 domain of SARS-CoV-2 S protein is amino acid residues 749-1353 of SEQ ID NO: 3. The S2' cleavage site occurs between amino acid residues R884 and S885. See Matsuyama et al., 2018, Journal of Virology 92(19): 1-12. In some embodiments, the antigen for hyperimmunization comprises or consists of the amino acid sequence of SEQ ID NO: 3, or an amino acid sequence having at least 80%, 85%, 90%, 95%, 96%, 97%, 98% or 99% sequence identity to SEQ ID NO: 3.

The amino acid sequence of the HKU1 S protein is provided herein as SEQ ID NO: 4. The S1/S2 cleavage site occurs between amino acid residues R756 and G757. Accordingly, the S1 domain of HKU1 S protein is amino acid residues 1-756 of SEQ ID NO: 4, and the S2 domain of HKU1 S protein is amino acid residues 757-1351 of SEQ ID NO: 4. The S2' cleavage site occurs between amino acid residues R900 and S901. See Matsuyama et al., 2018, Journal of Virology 92(19): 1-12. In some embodiments, the antigen for hyperimmunization comprises or consists of the amino acid sequence of SEQ ID NO: 4, or an amino acid sequence having at least 80%, 85%, 90%, 95%, 96%, 97%, 98% or 99% sequence identity to SEQ ID NO: 4.

The amino acid sequence of the NL63 S protein is provided herein as SEQ ID NO: 5. The S1/S2 junction occurs between amino acid residues V717 and S718. Accordingly, the S1 domain of NL63 S protein is amino acid residues 1-717 of SEQ ID NO: 5, and the S2 domain of NL63 S protein is amino acid residues 718-1356 of SEQ ID NO: 5. See Lin et al., 2008, Journal of General Virology 89: 1015-1024. In some embodiments, the antigen for hyperimmunization comprises or consists of the amino acid sequence of SEQ ID NO: 5, or an amino acid sequence having at least 80%, 85%, 90%, 95%, 96%, 97%, 98% or 99% sequence identity to SEQ ID NO: 5.

The amino acid sequence of the OC43 S protein is provided herein as SEQ ID NO: 6. The S1/S2 junction occurs between amino acid residues R757 and G758. Accordingly, the S1 domain of OC43 S protein is amino acid residues 1-757 of SEQ ID NO: 6, and the S2 domain of SARS-OC43 S protein is amino acid residues 758-1353 of SEQ ID NO: 6. See de Haan et al., 2008, Journal of Virology 82(12): 6078-6083. In some embodiments, the antigen for hyperimmunization comprises or consists of the amino acid sequence of SEQ ID NO: 6, or an amino acid sequence having at least 80%, 85%, 90%, 95%, 96%, 97%, 98% or 99% sequence identity to SEQ ID NO: 6.

The amino acid sequence of the 229E S protein is provided herein as SEQ ID NO: 7. The S1/S2 junction occurs between amino acid residues R567 and N568. Accordingly, the S1 domain of 229E S protein is amino acid residues 1-567 of SEQ ID NO: 7, and the S2 domain of 229E S protein is amino acid residues 568-1173 of SEQ ID NO: 7. See Bonnin et al., 2018, Journal of General Virology 99: 908-912. In some embodiments, the antigen for hyperimmunization comprises or consists of the amino acid sequence of SEQ ID NO: 7, or an amino acid sequence having at least 80%, 85%, 90%, 95%, 96%, 97%, 98% or 99% sequence identity to SEQ ID NO: 7.

Coronavirus N Protein

The coronavirus nucleocapsid (N) protein packages the positive strand viral genome RNA into a helical ribonucleocapsid (RNP) and plays a fundamental role during virion assembly through its interactions with the viral genome and membrane protein M. It also plays an important role in enhancing the efficiency of subgenomic viral RNA transcription as well as viral replication.

The amino acid sequence of the SARS-CoV-2 nucleocapsid (N) protein is provided herein as SEQ ID NO: 8. In some embodiments, the antigen for hyperimmunization comprises or consists of the amino acid sequence of SEQ ID NO: 9, or an amino acid sequence having at least 80%, 85%, 90%, 95%, 96%, 97%, 98% or 99% sequence identity to SEQ ID NO: 9.

The amino acid sequence of the SARS-CoV nucleocapsid (N) protein is provided herein as SEQ ID NO: 9. In some embodiments, the antigen for hyperimmunization comprises or consists of the amino acid sequence of SEQ ID NO: 9, or an amino acid sequence having at least 80%, 85%, 90%, 95%, 96%, 97%, 98% or 99% sequence identity to SEQ ID NO: 9.

The amino acid sequence of the MERS nucleocapsid (N) protein is provided herein as SEQ ID NO: 10. In some embodiments, the antigen for hyperimmunization comprises or consists of the amino acid sequence of SEQ ID NO: 10, or an amino acid sequence having at least 80%, 85%, 90%, 95%, 96%, 97%, 98% or 99% sequence identity to SEQ ID NO: 10.

The amino acid sequence of the HKU1 nucleocapsid (N) protein is provided herein as SEQ ID NO: 11. In some embodiments, the antigen for hyperimmunization comprises or consists of the amino acid sequence of SEQ ID NO: 11, or an amino acid sequence having at least 80%, 85%, 90%, 95%, 96%, 97%, 98% or 99% sequence identity to SEQ ID NO: 11.

The amino acid sequence of the NL63 nucleocapsid (N) protein is provided herein as SEQ ID NO: 12. In some embodiments, the antigen for hyperimmunization comprises or consists of the amino acid sequence of SEQ ID NO: 12, or an amino acid sequence having at least 80%, 85%, 90%, 95%, 96%, 97%, 98% or 99% sequence identity to SEQ ID NO: 12.

The amino acid sequence of the OC43 nucleocapsid (N) protein is provided herein as SEQ ID NO: 13. In some embodiments, the antigen for hyperimmunization comprises or consists of the amino acid sequence of SEQ ID NO: 13, or an amino acid sequence having at least 80%, 85%, 90%, 95%, 96%, 97%, 98% or 99% sequence identity to SEQ ID NO: 13.

The amino acid sequence of the 229E nucleocapsid (N) protein is provided herein as SEQ ID NO: 14. In some embodiments, the antigen for hyperimmunization comprises or consists of the amino acid sequence of SEQ ID NO: 14, or an amino acid sequence having at least 80%, 85%, 90%, 95%, 96%, 97%, 98% or 99% sequence identity to SEQ ID NO: 14.

Angiotensin converting enzyme 2 (ACE2) is the human receptor for SARS-CoV-2, SARS-CoV and the related human respiratory coronavirus NL63. ACE2 is a membrane-associated aminopeptidase expressed in vascular endothelia, renal and cardiovascular tissue, and epithelia of the small intestine and testes. A region of the extracellular portion of ACE2 that includes the first α-helix and lysine 353 and proximal residues of the N terminus of β-sheet 5 interacts with high affinity to the receptor binding domain of the SARS-CoV S glycoprotein. See Jia et al., 2005, J Virol. 79(23): 14614-14621; and Gralinski et al., cited above. Because ACE2 is involved in cellular entry for some human coronaviruses, administering antibodies to ACE2 to a subject can help to block entry of the virus into the host cell, preventing or reducing replication of the virus in the subject. The amino acid sequence of human ACE2 is provided herein as SEQ ID NO: 15. In some embodiments, the antigen for hyperimmunization comprises or consists of the amino acid sequence of SEQ ID NO: 15, or an amino acid sequence having at least 80%, 85%, 90%, 95%, 96%, 97%, 98% or 99% sequence identity to SEQ ID NO: 15.

In addition to coronavirus peptide sequences, the antigen used for hyperimmunization can further comprise a linker sequence (e.g., SEQ ID NO: 17) and a histidine tag (e.g., SEQ ID NO: 18) to aid in purification of the antigen. In some embodiments, the antigen is a SARS-CoV-2 S protein RBD further comprising a linker sequence and a histidine tag. In a particular embodiment, the antigen comprises or consists of the amino acid sequence of SEQ ID NO: 19, or an amino acid sequence having at least 80%, 85%, 90%, 95%, 96%, 97%, 98% or 99% sequence identity to SEQ ID NO: 19.

Hyperimmunization Procedure

The following list of steps is an example of a preferred procedure used to bring an egg-producing animal to a heightened state of immunity from which the resultant hyperimmune egg or egg product can be administered to an avian:
1. Selecting one or more antigens.
2. Eliciting an immune response in the egg-producing animal by primary immunization.
3. Administering booster vaccines of one or more antigens of appropriate dosage to induce and maintain the hyperimmune state.

Step 1: The critical point in this step is that the antigen(s) must be capable of inducing immune and hyperimmune states in the egg-producing animal. In some embodiments, the egg-producing animal is immunized with an antigen selected from:
 i) a human coronavirus spike (S) protein, a human coronavirus S1 subunit protein, a human coronavirus S2 subunit protein, a human coronavirus receptor binding domain (RBD), and an immunogenic fragment thereof;
 ii) a human coronavirus nucleocapsid (N) protein, and an immunogenic fragment thereof;
 iii) a human ACE2 receptor protein, and an immunogenic fragment thereof; and
 iv) a human coronavirus selected from the group consisting of SARS CoV-1, MERS, SARS-CoV-2, HCoV-HKU1, HCoV-NL63, HCoV-OC43 and HCoV-229E.

In some embodiments, the antigen comprises or consists of a human coronavirus RBD, e.g., a SARS-CoV-2 RBD, or an immunogenic fragment thereof.

Step 2: For SARS CoV-1, MERS, SARS-CoV-2, HCoV-HKU1, HCoV-NL63, HCoV-OC43 and HCoV-229E, the vaccine can be either a killed or live-attenuated virus. The vaccine can be administered by any method that elicits an immune response. It is preferred that immunization be accomplished by administering the vaccine through intramuscular or subcutaneous injection. The preferred muscle for injection in an avian is the breast muscle. Dosage is preferably 0.05-5 milligrams of the immunogenic vaccine. Other methods of administration that can be used include intravenous injection, intraperitoneal injection, intradermal, rectal suppository, aerosol or oral administration.

It can be determined whether the vaccine has elicited an immune response in the egg-producing animal through a number of methods known to those having skill in the art of immunology. Examples of these include enzyme-linked immunosorbent assays (ELISA), tests for the presence of antibodies to the stimulating antigens, and tests designed to evaluate the ability of immune cells from the host to respond to the antigen. The minimum dosage of antigen necessary to induce an immune response depends on the vaccination procedure used, including the type of adjuvants and formulation of antigen(s) used as well as the type of egg-producing animal used as the host.

Step 3: The hyperimmune state is preferably induced and maintained in the target animal by repeated booster administrations of an appropriate dosage at fixed time intervals. The time intervals are preferably one week to three month intervals over a period of 6-12 months. However, it is essential that the booster administrations do not lead to immune tolerance. Such processes are well known in the art. Methods of preparing the hyperimmunized egg product are described, for example, in U.S. Pat. No. 6,803,035, which is incorporated by reference herein in its entirety.

In some embodiments, an antigen as described herein is formulated with an adjuvant. The adjuvant can selected from among Freund's complete adjuvant, Freund's incomplete adjuvant, a saponin, a biodegradable polymer, aluminum hydroxide, mineral oil, a surfactant, and combinations thereof. Exemplary saponins include QS-21 and Quil A. Exemplary biodegradable polymers include chitosan, zymosan, a poly(ethylene glycol)-block-poly(propylene glycol)-block-poly(ethylene glycol), such as Pluronic® L121 block copolymer, poly(lactic acid), poly(glycolic acid), poly(lactic-co-glycolic acid), polycaprolactone, and combinations thereof. Exemplary surfactants include polysorbate 80 and sorbitan trioleate.

In a particular embodiment, an antigen as described herein is formulated into a Freund's vaccine. In some embodiments, an antigen as described herein is formulated with an adjuvant selected from the group consisting of Freund's complete adjuvant, Freund's incomplete adjuvant and QS21. In the first vaccination, the egg-producing animal receives two 0.5 ml doses of each antigen. Two weeks later, one 0.5 ml dose of each antigen is administered to the egg-producing animal as a booster vaccination. An additional booster vaccination is performed 4 weeks after the first vaccination. The vaccines can be administered to breast tissue.

It is possible to use other hyperimmunization maintenance procedures or combination of procedures, such as, for example, intramuscular injection for primary immunization and intravenous injection for booster injections. Further procedures include simultaneously administering microencapsulated and liquid antigen, or intramuscular injection for primary immunization, and booster dosages by oral administration or parenteral administration by microencapsulation means. Several combinations of primary and hyperimmunization are known to those skilled in the art.

In certain embodiments, the hyperimmunized egg product comprises antibodies to an antigen selected from:

i) a human coronavirus spike (S) protein, a human coronavirus S1 subunit protein, a human coronavirus S2 subunit protein, a human coronavirus receptor binding domain (RBD), and an immunogenic fragment thereof;
ii) a human coronavirus nucleocapsid (N) protein, and an immunogenic fragment thereof;
iii) a human ACE2 receptor protein, and an immunogenic fragment thereof; and
iv) a human coronavirus selected from the group consisting of SARS CoV-1, MERS, SARS-CoV-2, HCoV-HKU1, HCoV-NL63, HCoV-OC43 and HCoV-229E.

In some embodiments, the hyperimmunized egg product comprises antibodies to a human coronavirus receptor binding domain (RBD), e.g., a SARS-CoV-2 RBD, or an immunogenic fragment thereof.

The antibody can be an IgA, IgM or IgY antibody. In a particular embodiment, the antibody is an IgY antibody.

The hyperimmunized egg or hyperimmunized egg product can contain an increased level of an antibody (e.g., an IgY antibody) specific to a particular antigen disclosed herein relative to a control egg or control egg product obtained from an egg-producing animal that is not hyperimmunized with the particular antigen. For example, in some embodiments the hyperimmunized egg or hyperimmunized egg product contains an increased level of an antibody that is specific to an antigen selected from:

i) a human coronavirus spike (S) protein, a human coronavirus S1 subunit protein, a human coronavirus S2 subunit protein, a human coronavirus receptor binding domain (RBD), and an immunogenic fragment thereof;

ii) a human coronavirus nucleocapsid (N) protein, and an immunogenic fragment thereof;

iii) a human ACE2 receptor protein, and an immunogenic fragment thereof; and iv) a human coronavirus selected from the group consisting of SARS CoV-1, MERS, SARS-CoV-2, HCoV-HKU1, HCoV-NL63, HCoV-OC43 and HCoV-229E, relative to a control egg or egg product obtained from an egg-producing animal that is not hyperimmunized. In some embodiments, the hyperimmunized egg or hyperimmunized egg product contains an increased level of an antibody that is specific to a human coronavirus receptor binding domain (RBD), e.g., a SARS-CoV-2 RBD, or an immunogenic fragment thereof.

In some embodiments, the hyperimmunized egg or egg product comprises at least 10%, 20%, 30%, 40%, 50%, 100%, 200%, 300%, 400% or 500% more antibody (e.g. IgY antibody) specific to a particular antigen disclosed herein by weight relative to a control egg or control egg product obtained from an egg-producing animal that is not hyperimmunized with the particular antigen.

The hyperimmunized egg or hyperimmunized egg product can contain increased levels of antibodies to two or more of the antigens disclosed herein, relative to a control egg or control egg product obtained from an egg-producing animal that is not hyperimmunized.

Comparisons of antibody titers in hyperimmunized egg products and control egg products can be determined by methods known in the art. For example, in one embodiment, eggs are collected and the antibody titers are monitored by ELISA at regular intervals. To determine antibody titers, total IgY is extracted from eggs using Pierce™ Chicken IgY Purification Kit (Thermo Fisher Scientific, Waltham, MA). Briefly, 2 mL of egg is mixed with five volumes of delipidation reagent and IgY is purified following the manufacturer's instructions. Spray dried egg powder samples are reconstituted in sterile PBS at 1 mg/mL, and filtered through a 0.22 μm membrane filter. Specific antibody titers in the isolated IgY or egg powder samples are measured by ELISA. Flat bottom, 96-well microtiter plates (Corning® Costar®, Corning, NY) are coated with purified recombinant proteins (e.g. Antigens B, C, Co1, or Co2) at 10 μg/mL (100 μL/well) and incubated overnight at 4° C. The plates are washed twice with PBS containing 0.05% Tween 20 (Sigma-Aldrich, St. Louis, MO) and blocked with 100 μL/well of PBS containing 1% Bovine Serum Albumin (BSA) and incubated for 1 h at RT. Serially diluted (in PBS with 0.1% BSA) IgY samples from egg powder samples are added to the plates in triplicate wells (100 μL/well) and incubated for 2 h at RT with constant shaking. The plates are then washed with PBS-T and treated with peroxidase-conjugated rabbit anti-chicken IgY (IgG) antibody (1:500; Sigma), incubated for 30 min, followed by color development for 10 minutes with 0.01% tetramethylbenzidine substrate (Sigma) in 0.05 M Phosphate-Citrate buffer, pH 5.0. Bound antibodies are detected by measuring optical density at 450 nm ($OD_{450}$) using a microplate reader (Bio-Rad, Hercules, CA).

Antibody titers can be expressed by the highest fold dilution of egg product that still contains detectable antibodies as measured by optical density as described above. For example, an antibody titer of 1000 would indicate that a 1000-fold dilution of the egg product contains detectable antibody, but higher dilutions do not contain detectable antibody. In some embodiments, the antibody titer in the hyperimmunized egg product is at least 50,000, at least 80,000, at least 100,000, at least 160,000, at least 250,000, at least 320,000 at least 500,000, at least 640,00, or at least 1 million, 2 million, 3 million, 4 million, 5 million, 6 million, 7 million, 8 million, 9 million, 10 million, 11 million, 12 million, 13 million, 14 million, 15 million, 16 million, 17 million, 18 million, 19 million, or 20 million. In a particular embodiment, the antibody titer in the hyperimmunized egg product is at least 80,000.

In some embodiments, the hyperimmunized egg or egg product comprises at least 0.0001%, 0.0005%, 0.001%, 0.005%, 0.01%, 0.05%, or 0.1% by weight of an IgY antibody to a specific antigen disclosed herein. Typically, a whole chicken egg weighs approximately 60 grams without the shell, with the egg yolk weighing approximately 20 grams and the egg white weighing approximately 40 grams. In some embodiments, 3 grams of egg yolk contains approximately 20 grams of total IgY, such that a whole egg contains about 150-200 mg total IgY. In some embodiments, at least 1%, 2%, 3%, 4%, 5%, 6%, 7%, 8%, 9%, 10%, 11%, 12%, 13%, 14%, 15%, 16%, 17%, 18%, 19%, 20%, 25% or 30% of the total IgY in the hyperimmunized egg or egg product is specific to one of the antigens used for hyperimmunization.

Hyperimmunized eggs or egg products can contain an increased level of two or more antibodies (e.g. IgY antibodies), each of which is specific to a different antigen disclosed herein, relative to a control egg or egg product obtained from an egg-producing animal that is not hyperimmunized. The level of increase of each antibody (e.g. IgY antibody) in the hyperimmunized egg or egg product can be at least 10%, 20%, 30%, 40%, 50%, 100%, 200%, 300%, 400%, 500% or more by weight, relative to a control egg or egg product.

Compositions and Administration

In certain aspects, the present disclosure relates to a method for preventing or treating a coronavirus infection in a subject in need thereof, comprising administering to the subject a therapeutically effective amount of a hyperimmunized egg product obtained from an egg-producing animal, thereby preventing or treating coronavirus infection in the subject, wherein the hyperimmunized egg product comprises a therapeutically effective amount of one or more antibodies to the coronavirus.

Once the egg-producing animals have been sufficiently hyperimmunized, it is preferred that the eggs from these animals are collected and processed to produce a hyperimmunized egg product in administrable form. The hyperimmunized egg product can be prepared by dehydration, spray drying, or freeze drying of whole egg, yolk or purified IgY fraction. The dried hyperimmunized egg product can be mixed with an agent such as silicon or silicon derivatives that improves flow properties. The dried hyperimmunized egg product can comprise a desiccant. The hyperimmunized egg product can be stored at ambient temperature or refrigerated, for example, at 4° C.

In some embodiments the hyperimmunized egg product is encapsulated. Methods of encapsulating antibodies and other proteins are known in the art and are described, for example, in U.S. Pat. No. 7,105,158. Materials that are biodegradable and nonantigenic can be used as the encapsulating material. Encapsulating materials include, but are not limited to albumin, PLGA, globulin, natural and synthetic polymers, and thermoplastic polymers. Any polymer that is biocompatible and bioerodible can be used for encapsulation. A number of available crosslinking agents such as glutaraldehyde can be used to crosslink the encapsulating material. Additionally, the pharmaceutically delivered material can contain microspheres of encapsulated drug whereby the microspheres have different concentrations of crosslinking agent used, thereby creating a prolonged continuous release of the drug.

In some embodiments, the hyperimmunized egg product is in the form of a microparticle or nanoparticle, for example, an encapsulated microparticle or encapsulated nanoparticle. The microparticles and nanoparticles can have any shape. Typically the microparticles and nanoparticles are spherical. Other suitable shapes include, but are not limited to, flakes, triangles, ovals, rods, polygons, needles, tubes, cubes and cuboid structures. In certain embodiments, the microparticles have a diameter of less than 10, 9, 8, 7, 6, 5, 4, 3, 2, 1, 0.9, 0.8, 0.7, 0.6, 0.5, 0.4, 0.3, 0.2 or 0.1 micron(s). Any of these values can be used to define a range for the diameter of the microparticle. For example the diameter of the microparticle can be from about 0.1 to about 10 microns, from about 0.1 to about 1 micron, or from about 0.1 to about 2 microns. In other embodiments, larger microparticles or particles can be used. For example the microparticles can have a diameter ranging from 10 microns to 1000 microns. In certain embodiments, the nanoparticles have a diameter of less than 1000, 900, 800, 700, 600, 500, 400, 300, 200, 100, or 10 nm. Any of these values can be used to define a range for the diameter of the nanoparticle. For example the diameter of the nanoparticle can be from about 10 to about 1000 nm, from about 100 to about 1000 nm, or from about 10 to about 100 nm.

There are several processes whereby microparticles or nanoparticles can be encapsulated, including, for example, multi-walled microencapsulation, hot melt encapsulation, phase separation encapsulation, spontaneous emulsion, solvent evaporation microencapsulation, solvent removal microencapsulation, and coacervation. These methods are known in the art. Detailed descriptions of the methods are discussed in Mathiowitz et al., "Microencapsulation", in Encyclopedia of Controlled Drug Delivery, vol. 2, pp. 495-546, 1999, John Wiley & Sons, Inc. New York, N.Y., which is incorporated by reference herein in its entirety.

In some embodiments, the IgY antibody specific for an antigen disclosed herein is administered to the subject in a concentrated form. For example, in some embodiments, the IgY antibody is purified or partially purified and concentrated before administration to the subject. Methods of purifying and concentrating IgY antibodies from egg products are known in the art and are described, for example, in U.S. Pat. No. 5,367,054, which is incorporated by reference herein in its entirety.

In some embodiments, the hyperimmunized egg products described herein are used to treat coronavirus infection in a subject that has been infected with the coronavirus. In some embodiments, the subject has symptoms of coronavirus infection, e.g. fever, cough, shortness of breath, headache, and/or diarrhea. In some embodiments, the subject has Severe Acute Respiratory Syndrome (SARS), Middle East Respiratory Syndrome (MERS) or Coronavirus Disease-2019 (COVID-19) at the time of administration of the hyperimmunized egg product.

In some embodiments, the hyperimmunized egg products described herein are used to prevent coronavirus infection in a subject. For example, in some embodiments, the subject is not infected with coronavirus at the time of administration of the hyperimmunized egg product. In some embodiments, the hyperimmunized egg products described herein are used to prevent or reduce the development of symptoms resulting from coronavirus infection. For example, in some embodiments, the subject is infected with coronavirus, but is not yet exhibiting symptoms of coronavirus infection at the time of administration of the hyperimmunized egg product.

In a particular embodiment, the subject to which the hyperimmunized egg product is administered is a human. In a particular embodiment, the coronavirus is a coronavirus that infects humans.

The hyperimmunized egg product of the present invention is administered to a subject (e.g. a human) by any means that treats or prevents coronavirus infection in the subject. In certain embodiments, administration occurs by oral administration or by inhalation. In certain embodiments, the hyperimmunized egg product is administered to the subject as an oral rinse, by inhalation, or by nasal drops or eye drops. In a particular embodiment, the hyperimmunized egg product is administered as an oral rinse. Egg and egg yolk are natural food ingredients and are non-toxic and safe. In other embodiments, the hyperimmunized egg product can be administered by injection, for example, intravenous, subcutaneous, or intramuscular injection. In a particular embodiment, the hyperimmunized egg product is purified or partially purified IgY that is administered by intravenous injection. Any of several known pharmaceutically acceptable carriers can be used in the preparation of an injectable or otherwise administrable preparation, including phosphate buffered saline, saline, ethanol, propylene glycol and the like.

In some embodiments, the pharmaceutically acceptable carrier comprises a compound that is generally recognized as safe (GRAS) by the FDA. In some embodiments, the GRAS compound is selected from acetic acid, aconitic acid, adipic acid, alginic acid, α-amylase enzyme preparation from *Bacillus stearothermophilus*, benzoic acid, bromelain, caprylic acid, mixed carbohydrase and protease enzyme product, citric acid, catalase (bovine liver), lactic acid, enzyme-modified lecithin, linoleic acid, malic acid, potassium acid tartrate, propionic acid, stearic acid, succinic acid, sulfuric acid, tannic acid, tartaric acid, diacetyl tartaric acid esters of mono- and diglycerides, agar-agar, brown algae, red algae, ammonium alginate, ammonium bicarbonate, ammonium carbonate, ammonium chloride, ammonium hydroxide, ammonium citrate, dibasic, ammonium phosphate (monobasic), ammonium phosphate (dibasic), ammonium sulfate, bacterially-derived carbohydrase enzyme preparation, bacterially-derived protease enzyme preparation, bentonite, benzoyl peroxide, n-butane and iso-butane, calcium acetate, calcium alginate, calcium carbonate, calcium chloride, calcium citrate, calcium gluconate, calcium glycerophosphate, calcium hydroxide, calcium iodate, calcium lactate, calcium oxide, calcium pantothenate, calcium propionate, calcium stearate, calcium sulfate, carbon dioxide, beta-carotene, cellulase enzyme preparation derived from *Trichoderma longibrachiatum*, clove and its derivatives, cocoa butter substitute, copper gluconate, copper sulfate, corn silk and corn silk extract, cuprous iodide, L-cysteine, L-cysteine monohydrochloride, dextrin, diacetyl, dill and its derivatives, enzyme-modified fat, ethyl alcohol, ethyl formate, ferric ammonium citrate, ferric chloride, ferric citrate, ferric phosphate, ferric pyrophosphate, ferric sulfate, ferrous ascorbate, ferrous carbonate, ferrous citrate, ferrous fumarate, ferrous gluconate, ferrous lactate, ferrous sulfate, ficin, garlic and its derivatives, glucono delta-lactone, corn gluten, wheat gluten, glyceryl monooleate, glyceryl monostearate, glyceryl behenate, glyceryl palmitostearate, acacia (gum arabic), gum ghatti, guar gum, locust (carob) bean gum, karaya gum (sterculia gum), gum tragacanth, helium, hydrogen peroxide, inositol, insoluble glucose isomerase enzyme preparations, iron, elemental, isopropyl citrate, lactase enzyme preparation from *Candida pseudotropicalis*, lactase enzyme preparation from *Kluyveromyces lactis*, lecithin, licorice and licorice derivatives, ground limestone, animal lipase, lipase enzyme preparation derived from *Rhizopus niveus*, magnesium carbonate, magnesium chloride, magnesium hydroxide, magnesium oxide, magnesium phosphate, magnesium stearate, magnesium sulfate, malt, maltodextrin, malt syrup (malt extract), manganese chloride, manganese citrate, manganese gluconate, manganese sulfate, menhaden oil, methylparaben, microparticulated protein product, monk fruit sweetener, mono- and diglycerides, monosodium phosphate derivatives of mono- and diglycerides, niacin, niacinamide, nickel, nisin preparation, nitrogen, nitrous oxide, peptones, rapeseed oil, ox bile extract, ozone, pancreatin, papain, pectins, pepsin, potassium alginate, potassium bicarbonate, potassium carbonate, potassium chloride, potassium citrate, potassium hydroxide, potassium iodide, potassium iodate, potassium lactate, potassium sulfate, propane, propyl gallate, propylene glycol, propylparaben, pyridoxine hydrochloride, rennet (animal-derived) and chymosin preparation (fermentation-derived), riboflavin, riboflavin-5-phosphate (sodium), rue, Oil of rue, shea nut oil, sodium acetate, sodium alginate, sodium benzoate, sodium bicarbonate, sodium carbonate, sodium citrate, sodium diacetate, sodium hydroxide, sodium hypophosphite, sodium lactate, sodium metasilicate, sodium propionate, sodium sesquicarbonate, sodium tartrate, sodium potassium tartrate, sodium thiosulfate, sorbitol, stannous chloride (anhydrous and dihydrated), starter distillate, stearyl citrate, *stevia*, sucralose, sucrose, sorn sugar, invert sugar, corn syrup, high fructose corn syrup, thiamine hydrochloride, thiamine mononitrate, α-tocopherols, triacetin, tributyrin, triethyl citrate, trypsin, urea, urease enzyme preparation from *Lactobacillus fermentum*, vitamin A, vitamin B12, vitamin D, beeswax (yellow and white), candelilla wax, carnauba wax, whey, reduced lactose whey, reduced minerals whey, whey protein concentrate, whey protein isolate, Baker's yeast extract, zein, and aminopeptidase enzyme preparation derived from *Lactococcus lactis*.

In some embodiments, the hyperimmunized egg product is administered through drinking water. In some embodiments, the hyperimmunized egg product is administered as a beverage, e.g., a beverage comprising one or more flavoring agents, coloring agents and/or sweeteners. In certain embodiments, the hyperimmunized egg product is administered as a composition comprising one or more additional compounds, e.g. a nutrient or probiotic. For example, in one embodiment, the hyperimmunized egg product of the invention is integrated into a dietary supplement. One method for preparing the egg of the invention to be incorporated into a dietary supplement involves drying the egg into an egg powder. Although various methods are known for drying eggs, spray drying is a preferred method. The process of spray drying eggs is well known in the art. In some embodiments, the composition is an aqueous solution comprising the hyperimmunized egg product. In some embodiments, the hyperimmunized egg product is a liquid, a freeze-dried powder, or formulated to be administered as a spray.

In certain embodiments, whole eggs are divided into separate fractions such as egg yolks and egg whites. For example, it is generally known in the art that IgY antibody is found in egg yolks. Accordingly, those having ordinary skill in the art would clearly recognize that separation of egg yolks could provide more potent fractions or elimination of undesirable components, and would allow for other modes of administration such as administering hyperimmunized egg product parenterally, subcutaneously, intravenously, intramuscularly, intraperitoneally, intranasally, intraocularly, orally or topically. Such further separation will provide for the ability to make encapsulated products and compositions comprising said egg or fraction thereof.

The hyperimmune egg product is preferably administered to the subject in an amount that is immunologically effective in treating or preventing coronavirus infection. Dosage and duration of the administration will depend upon the particular condition of the subject. In some embodiments, the hyperimmunized egg product is administered to the subject for at least 5, 6, 7, 8, 9, 10, 11, 12, 13, 14, 15, 20, 25, 30, 60, 90, 180 or 365 days. The hyperimmunized egg product can be administered to the subject 1, 2, 3, 4, 5, 6, 7, 8, 9, 10 or more times per day. Any of these values can be used to define a range for the number of times the hyperimmunized egg product can be administered to the subject per day. For example, in some embodiments the hyperimmunized egg product is administered to the subject 1-2 times per day, 1-3 times per day, or 1-4 times per day. In some embodiments, the hyperimmunized egg product is administered to the subject at least twice per day. In some embodiments, the hyperimmunized egg product is administered to subject at least once per day. In some embodiments, the hyperimmunized egg product is administered to the subject daily. In some embodiments, the hyperimmunized egg product is administered to the subject once every two days. In some embodiments, the hyperimmunized egg product is administered to the subject once every three days. In some embodiments, the hyperimmunized egg product is administered to the subject once per week. In a particular embodiment, the hyperimmunized egg product is administered to the subject once per day for more than 10 consecutive days.

In some embodiments, daily amounts ranging from less than one to several whole, hyperimmune eggs (or hyperimmune egg products containing the equivalent of less than one to several whole, hyperimmune eggs) can be administered to the subject depending on the particular circumstance of the condition. More potent fractions can be separated and concentrated by methods well-known in the art, from several hundred eggs.

In certain embodiments, the effective amount of the hyperimmunized egg product administered to a subject (e.g. a human) is 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day. For example, in some embodiments, 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day of whole egg are administered to the subject. In some embodiments, 0.1, 0.2, 0.3, 0.4, 0.5, 0.6, 0.7, 0.8, 0.9, 1, 2, 3, 4, 5, 6, 7, 8, 9, 10, 20, 30, 40 or 50 grams per day of egg yolk are administered to the subject. In some embodiments, 0.1, 0.2, 0.3, 0.4, 0.5, 0.6, 0.7, 0.8, 0.9, 1, 2, 3, 4, 5, 6, 7, 8, 9 or 10 grams per day of dried egg yolk or dried whole egg are administered to the subject. Any of these values can be used to define a range for the effective amount of the hyperimmunized egg product administered to the mammal. For example, in some embodiments the effect amount of the hyperimmunized egg product is between 0.1 and 10 grams, between 0.5 to 6 grams, or between 1 and 5 grams per day. In a particular embodiment, 3 grams of egg yolk are administered to the subject (e.g. a human) per day.

In certain embodiments, the composition comprises at least 0.01%, 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 96%, 97%, 98% or 99% w/w of the hyperimmunized egg product. Any of these values can be used to define a range for the concentration of the hyperimmunized egg product in the composition. For example, in some embodiments, the composition comprises between 0.01% and 50%, between 0.1% and 50%, or between 1% and 50% w/w of the hyperimmunized egg product.

In some embodiments, the hyperimmunized egg product is administered to a subject in combination with one or more additional therapeutic agents. In some embodiments, the one or more additional therapeutic agents comprise one or more antibodies (e.g., one or more monoclonal antibodies) that specifically bind to SARS-CoV-2. In some embodiments, the one or more monoclonal antibodies bind the RBD of the S protein of SARS-CoV-2. In some embodiments, the additional therapeutic agent is a compound (e.g., a small molecule or peptide) that interferes with entry of the coronavirus (e.g., SARS-CoV-2) into a human cell. In some embodiments, the additional therapeutic agent is a compound (e.g., a small molecule or peptide) that interferes with replication of the coronavirus (e.g., SARS-CoV-2) in a human cell. In some embodiments, the additional therapeutic agent is an antiviral agent, an anti-inflammatory agent, a steroid, or an anti-thrombotic agent. In some embodiments, the antiviral agent is selected from the group consisting of remdesivir, lopinavir and flapinavir.

Description of Sequences

| SEQ ID NO: | Description |
|---|---|
| 1 | Amino acid sequence of the SARS-CoV-2 spike (S) protein |
| 2 | Amino acid sequence of the SARS-CoV S protein |
| 3 | Amino acid sequence of the MERS S protein |
| 4 | Amino acid sequence of the HKU1 S protein |
| 5 | Amino acid sequence of the NL63 S protein |
| 6 | Amino acid sequence of the OC43 S protein |
| 7 | Amino acid sequence of the 229E S protein |
| 8 | Amino acid sequence of the SARS-CoV-2 nucleocapsid (N) protein |
| 9 | Amino acid sequence of the SARS-CoV nucleocapsid (N) protein |
| 10 | Amino acid sequence of the MERS nucleocapsid (N) protein |
| 11 | Amino acid sequence of the HKU1 nucleocapsid (N) protein |
| 12 | Amino acid sequence of the NL63 nucleocapsid (N) protein |
| 13 | Amino acid sequence of the OC43 nucleocapsid (N) protein |
| 14 | Amino acid sequence of the 229E nucleocapsid (N) protein |
| 15 | Amino acid sequence of human ACE2 |
| 16 | Amino acid sequence of the RBD domain within the spike protein 1 of the native strain of SARS-CoV-2 |
| 17 | Linker in the RBD recombinant peptide used for hyperimmunization |
| 18 | Histidine tag in the RBD recombinant protein used for hyperimmunization |
| 19 | RBD recombinant peptide used for hyperimmunization, contains the linker and histidine tag |

EXAMPLES

Example 1. Preparation and Evaluation of Anti-RBD IgY Antibodies

1. SARS-CoV-2 Spike Protein 1 RBD Domain Used to Create a Peptide Antigen for Chicken Immunization The amino acid sequence of the RBD domain (SEQ ID NO: 16) within the spike protein 1 of the native strain of SARS-CoV-2 was used to create an RBD peptide for chicken immunization to raise IgY antibodies. A linker (GGSGGGSGGGS, SEQ ID NO: 17) and histidine tag (HHHHHH: SEQ ID NO: 18) were added to the C-terminus of the RBD domain, as shown below.

```
                                          (SEQ ID NO: 19)
VFNATRFASV YAWNRKRISN CVADYSVLYN SASFSTFKCY

GVSPTKLNDL CFTNVYADSF VIRGDEVRQI APGQTGKIAD

YNYKLPDDFT GCVIAWNSNN LDSKVGGNYN YLYRLFRKSN

LKPFERDIST EIYQAGSTPC NGVEGFNCYF PLQSYGFQPT

NGVGYQPYRV VVLSFELLHA PATVCGPKKS TNLVKNKCVN

FNFNGLTGTG VLTESNKKFL PFQQFGRDIA DTTDAVRDPQ

TLEILDITPC SFGGVSVITP GTNTSNQVAV LYQDVNCTEV

PVAIHADQLT PTWRVYSTGS NVFQ GGSGGGSGGGSHHHHHH
```

2. SDS PAGE Analysis of CHO Cell Expressed Recombinant RBD Peptide

A CHO expression system was used to express and purify the recombinant His tagged RBD domain which was then used for hyperimmunization. FIG. 1 shows the purity of the RBD peptide obtained (>90% purity) as determined by a Coomassie-stained 12% Reducing Tris-Glycine SDS-PAGE.

3. Immunization of Chickens with Recombinant RBD and Harvesting of Anti-RBD IgY from Egg Yolk The RBD domain peptide described above was used to vaccinate chickens. The chickens received several booster shots of the peptide to achieve high titers of anti-RBD IgY in the eggs laid by the chickens using a protocol similar to one described previously (see Yang et al., African Journal of Biotechnology Vol. 10(41), pp. 8146-8150). Before processing of the egg yolk or whole egg, the *Salmonella* and yeast contaminants in the solution were sterilized by heat treatment. The sterilization temperature was 61° C. and the sterilization time was 3 to 5 minutes.

IgY titer was determined by ELISA using partially (>85%) purified total IgYs from egg yolk.

Figure 2:
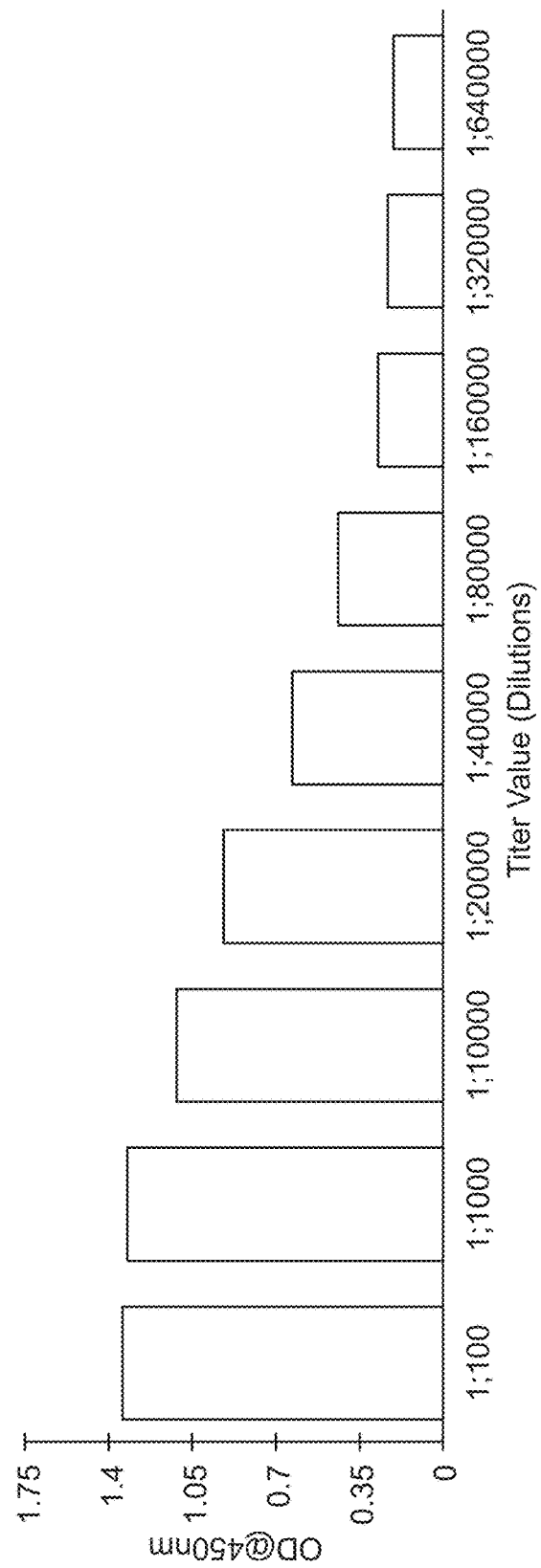
FIG. 2 shows anti-RBD IgY binding titer values obtained in an ELISA assay using a purified IgY fraction from egg yolk against native RBD.

ELISA was carried out by the standard protocol. Briefly, RBD peptide (1 µg) was coated on the plate, and anti-RBD IgY preparation from egg yolk was diluted as shown and applied to the plate to bind RBD peptide. The plate was blocked and washed following each addition as per standard ELISA protocol. The color was developed by complexing HRP-conjugated anti-IgY antibody and HRP standard as per standard ELISA protocols. The results demonstrate that high titers of IgY antibodies (>80,000 dilution also shows signal twice above background OD) were obtained against RBD immunized chicken egg yolk (see Table 1 below and FIG. 2). These results indicate that the IgYs have strong cross reactivity towards RBD. The >85% purified IgY fraction from egg yolk was then used for all experiments shown below.

TABLE 1

Titer values obtained in I-ELISA assay

| | 1; 100 | 1; 1000 | 1; 10000 | 1; 20000 | 1; 40000 | 1; 80000 | 1; 160000 | 1; 320000 | 1; 640000 | PC | CPC | NC |
|---|---|---|---|---|---|---|---|---|---|---|---|---|
| | 1 | 2 | 3 | 4 | 5 | 6 | 7 | 8 | 9 | 10 | 11 | 12 |
| A | 1.341 | 1.295 | 1.093 | 0.893 | 0.635 | 0.452 | 0.277 | 0.237 | 0.188 | 1.329 | 0.192 | 0.168 |
| B | 1.359 | 1.357 | 1.136 | 0.956 | 0.627 | 0.434 | 0.268 | 0.243 | 0.233 | 1.426 | 0.197 | 0.183 |

PC = positive control where a known antigen X was coated on the plate and anti-X-IgY was applied to bind to antigen X.
CPC = Only anti-RBD or anti-X antibodies were applied. No antigen.
NC = Antigen X was coated on the plate and anti-RBD IgY antibodies were applied to check for any cross reactivity.

Example 2. Measurement of Neutralizing Activity of Anti-RBD IgY Antibodies by ELISA and Dot Blot Assays Two separate methods were used to characterize the neutralizing activity of the anti-RBD IgY: 1) a commercially available competition ELISA assay from Genscript, USA, and
2) a dot blot assay in which the nitrocellulose membrane was coated with ACE2 and biotinylated RBD was used to monitor the binding (Saxena et al., bioRxiv, doi: 10.1101/2021.05.02.442384. 2021).

SARS-CoV2 enters human host cells using the receptor binding domain (RBD) on its surface spike protein. RBD directly binds to angiotensin receptor 2 (ACE2) present on human cells such as lung epithelium cells. SARS-CoV2 vaccines work by eliciting neutralizing antibodies which interfere with this binding, with the end result that the virus cannot enter the human cells.

We have designed a cell free dot blot competition assay to measure the binding of biotinylated RBD (B-RBD) to human ACE2 using a simple and rapid nitrocellulose membrane assay. Briefly, ACE2 was deposited on the membrane and B-RBD was added to it, and bound B-RBD was detected by adding streptavidin-HRP followed by HRP detection substrate. When the assay is performed in the presence of RBD neutralizing antibody, the amount of B-RBD bound to ACE-2 is reduced in proportion to the presence of neutralizing antibodies. Persons who are infected and those who are vaccinated against SARS-CoV2 produce an immune responses to the viral proteins, including the RBD of the S1 protein. Antibodies that bind RBD and block RBD's ability to bind ACE2 are neutralizing antibodies, and these are believed to be responsible for preventing viral infection and reducing the onset and severity of the disease.

Using this assay, anti-COVID-19 neutralizing antibodies can be tested in multiple body fluids such as blood, saliva and others. Laboratory-based tests using serum isolated from blood of subjects have received EUA (Emergency Use Authorization) from various regulatory bodies to screen for the presence of neutralizing antibodies, the levels of which are indicative of protection from COVID-19. We used this assay to evaluate the effectiveness of the anti-RBD IgY in neutralizing RBD-ACE2 binding following administration to subjects. The test is able to qualitatively and semi-quantitatively measure RBD binding to ACE2, and IgY's ability to neutralize the binding, which is indicative of performance. The dot blot is a competitive assay wherein higher neutralizing activity results in lower blot color formation. The dot blot stain color intensity was captured and quantitated using ImageJ software analysis.

Results

Figure 3:
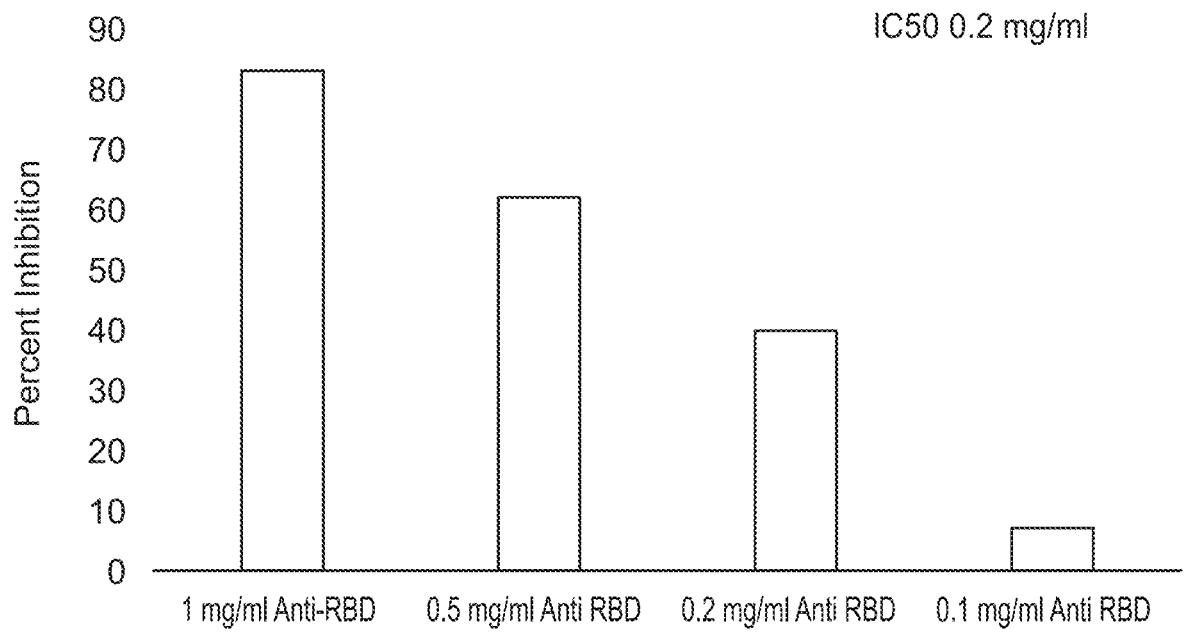
FIG. 3 shows inhibition of ACE2 binding to native RBD by IgY at various concentrations using ELISA and dot blot assays.
Figure 3:
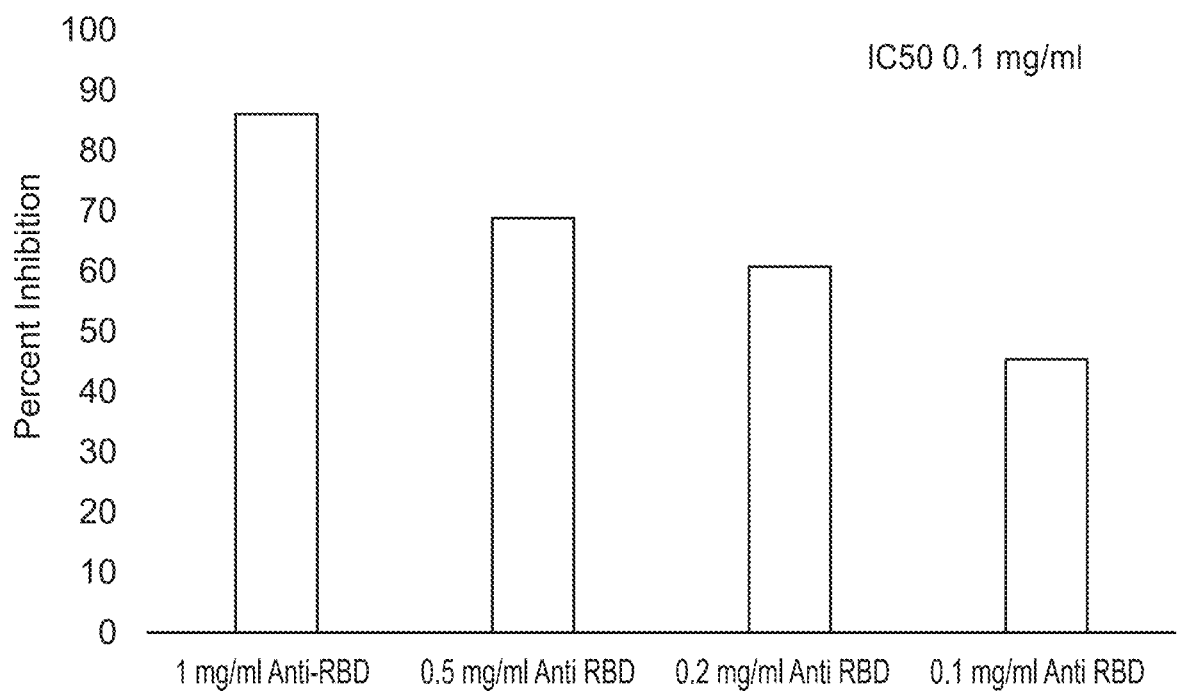

As shown in FIG. 3, a comparison of the two methods shows similar neutralizing activity by the two assays. Using a concentration curve, we were able to determine that the anti-RBD IgY inhibited the binding of RBD to ACE2 similarly with $IC_{50}$ of inhibition being 0.2 mg/ml in the ELISA assay and 0.1 mg/ml in the dot blot assay.

The Delta strain of SARS-CoV-2 virus previously emerged as a dominant strain. The Delta variant RBD is mutated with three amino acid changes from the native RBD. These mutations make this variant more transmissible and infective relative to the native strain. We tested whether the IgY antibody raised as above will a) bind to delta RBD and b) neutralize the binding of Delta RBD to ACE2 using ELISA and dot blot assays respectively.

Figure 4:
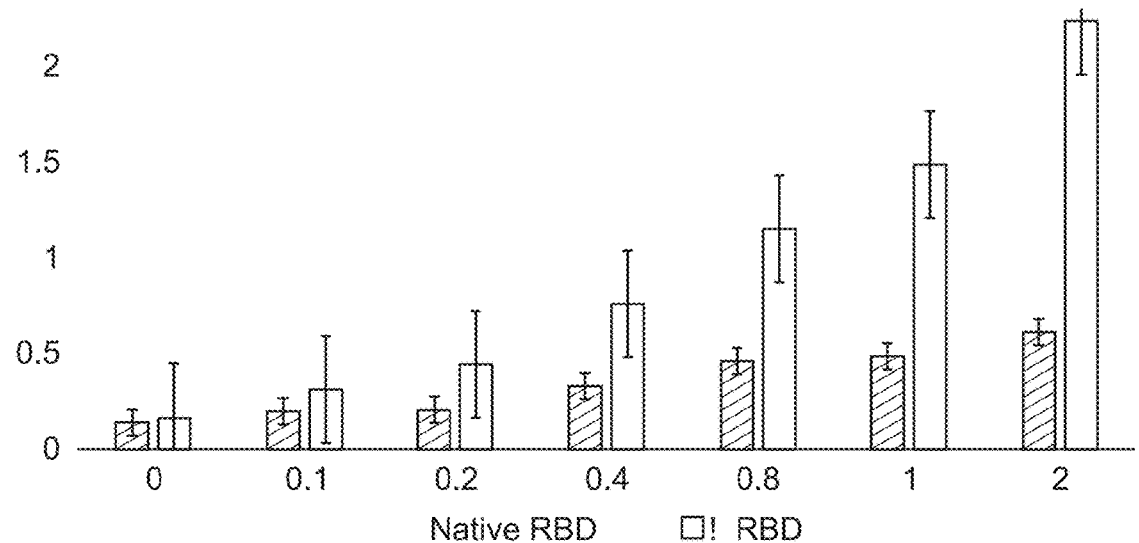
FIG. 4 shows binding of various concentrations of anti-RBD IgY to either native or delta RBD coated on the ELISA plate at 2 µg/ml. The bound IgY was detected using an anti-IgY HRP conjugated antibody and the binding is shown as OD at 405 nm.

FIG. 4 shows a head to head comparison of direct binding of the anti-RBD IgY to either native or Delta RBD (obtained commercially from Pentavalent Biosciences Private Limited, India) coated on an ELISA plate. Bound IgY was detected using and biotinylated anti-IgY antibody. As shown in FIG. 4, the IgY bound directly to both native and Delta RBD effectively at various concentrations, with binding to Delta RBD being almost 4-fold higher, suggesting that the IgY strongly recognizes Delta variant RBD.

Figure 5:
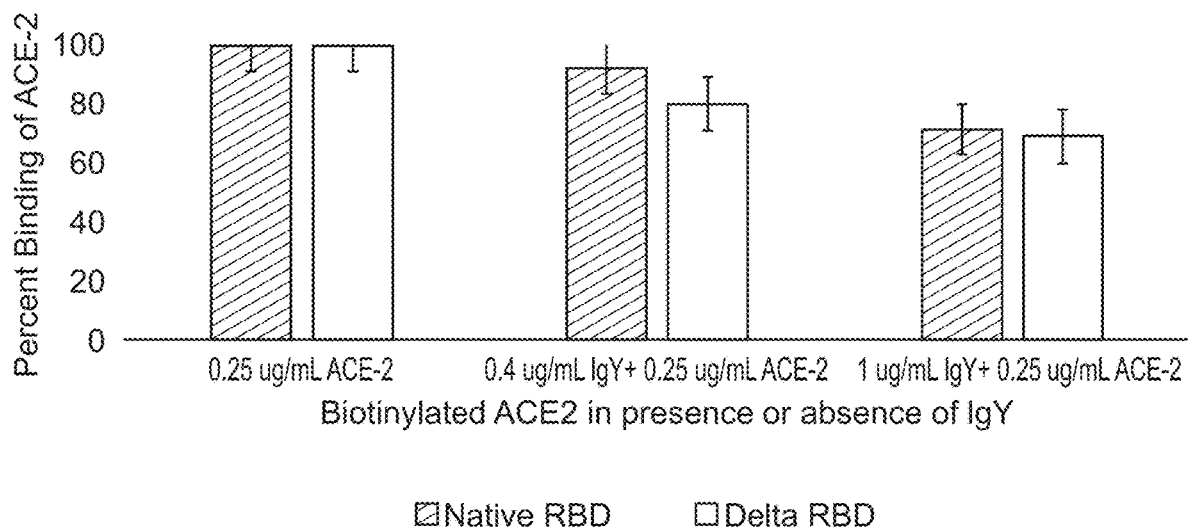
FIG. 5 shows binding of biotinylated ACE to native or Delta variant RBD in a dot blot assay in the presence or absence of anti-RBD IgY. Data is shown as percent of biotinylated ACE2 binding (100%).

Using the dot blot assay, we also determined if the IgY antibody of the invention can inhibit the binding of ACE2 to delta RBD. As shown in FIG. 5, at the concentrations of IgY used (1 µg/ml and 0.4 µg/ml) we found that IgY antibody inhibited biotinylated ACE2 interaction with both native RBD (91% and 75% ACE2 binding at 0.4 and 1 µg/ml IgY) and Delta RBD (75% and 69% ACE 2 binding at 0.4 and 1 µg/ml IgY), suggesting its utility in neutralizing Delta RBD binding to ACE2.

Example 3. Evaluation of Anti-RBD IgY in a Plaque Reduction Neutralization Test (PRNT)

The effect of the anti-RBD IgY described in Example 1 against SARS-CoV-2 was also examined in Vero cells (a monkey kidney cell line) in a plaque reduction neutralization test (PRNT). Since the anti-RBD IgY neutralize the binding of RBD to ACE2, we determined whether anti-RBD IgY reduces viral entry into the cells.

Viral Neutralization Assay

The primary aim of this study was to determine if the semi-purified anti-RBD IgY described in Example 1 was able to neutralize SARS-CoV2 and prevent the virus from entering Vero cells and subsequently reduce plaque formation.

The protocol was followed according to WHO guidelines. Briefly, the antibody samples were diluted sequentially 2-fold, up to 6 dilutions, and then incubated with equal volumes SARS-CoV2 (Wuhan strain) in a 1:1 ratio, and this mixture was allowed to incubate for 1 hr at 37° C. and then added onto the Vero cell monolayer and further incubated for 24 hrs at 37° C. Virus without any antibody served as a positive control for plaque formation. The number of plaques (pfu) formed with the control was compared with the plaque numbers obtained by pre-incubation of virus with various concentrations of antibody. Plaques were counted manually and % neutralization was calculated. Data was reported as $PRNT_{50}$, which represent the value of antibody concentration that is able to reduce the number of observed viral plaques by 50%, i.e., to neutralize 50% of the SARS CoV-2 virus utilized in the assay.

TABLE 2

Samples Used for the Viral Neutralization assay

| | |
|---|---|
| Sample 1 | Phosphate buffered saline ONLY |
| Sample 2 | 5 mg of semi purified anti-RBD IgY in 100 mL Phosphate buffered saline |
| Sample 3 | 1 mg of semi purified anti-RBD IgY in 100 mL Phosphate buffered saline |

Results

Table 3 below shows that at the two concentrations tested, IgY was able to reduce plaque formation effectively, suggesting its effectiveness in reducing virus binding and entry into Vero cells. Specifically, Sample 1 (control) was not able to neutralize SARS-CoV2 virus, whereas samples 2 and 3 (anti-RBD IgY) were able to neutralize SARS-CoV2 virus with $PRNT_{50}$ values of 4.61 and 1.28 IU/ml respectively. Thus, the viral neutralization assays clearly showed that the semi-purified anti-RBD IgY was able to neutralize SARS-CoV2 Wuhan strain in a dose dependent manner.

TABLE 3

Neutralization of SARS-CoV2 as determined by the plaque reduction neutralization test (PRNT)

| Sample No. | $PRNT_{50}$ (IU/ml) | Result (Positive or Negative) |
|---|---|---|
| 1 | NA | Negative |
| 2 | 4.61 | Positive |
| 3 | 1.28 | Positive |

Figure 7:
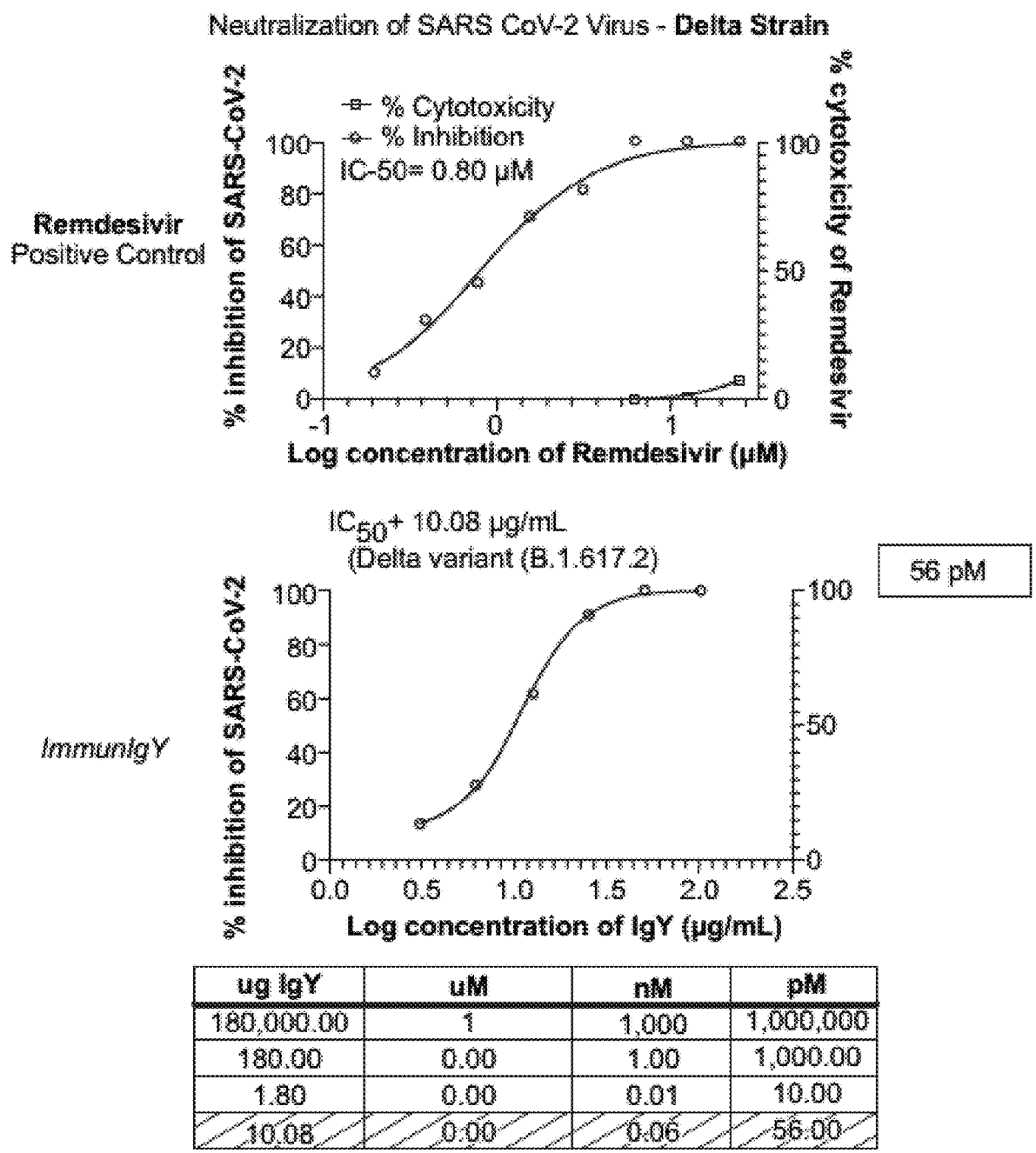
FIG. 7 shows the neutralizing activity of an oral rinse of an anti-RBD IgY antibody containing drink in a volunteer that received a single shot of a SARS-CoV2 vaccine.

Additional studies were conducted to determine the effect of the anti-RBD IgY on neutralization of the Wuhan strain and Delta strain of SARS-CoV2 using the PRNT assay described above. Remdesivir was used as a positive control. The results for the Wuhan strain are shown in FIG. 6, and the results for the Delta strain are shown in FIG. 7. The results demonstrate that the anti-RBD IgY antibodies were able to neutralize the SARS CoV-2 variants to the same extent in a Viral PRNT assay. The results suggest that the polyclonal nature of the anti-RBD IgY antibodies allows the antibodies to be broad-spectrum antibodies with the ability to neutralize the native and delta variant RBD.

Example 4. Evaluation of Anti-RBD IgY in a Human Clinical Trial

The primary objective of the study was to evaluate the effectiveness of anti-RBD IgY (IMMUNIGY-Vistop) in neutralizing RBD-ACE2 following administration to subjects.

| Study Protocol | |
|---|---|
| Protocol Title | A Study to Evaluate the Effectiveness of IMMUNIGY-Vistop (a formulated oral IgY product containing Anti-RBD IgY) in neutralizing the binding of RBD of the viral protein S1 to ACE2 human cellular receptor in Human Saliva and at various times following administration of IMMUNIGY-VISTOP (IMMUNIGY) to subjects. |
| Sponsor | Lay Sciences, Inc., Jupiter FL. USA |
| Study Sites | Reagene Biosciences Laboratories, Hyderabad, India |
| Study Phase and Design | Development Phase Prospective Open label pilot study |
| Study Medication | IMMUNIGY is a powder formulated for oral dosing following dissolution in water (1 gm in 20 mL) |
| Comparator | Subjects' saliva prior to administration with IMMUNIGY |
| Safety Evaluation Points | Any reports of oral and GI discomfort over a 24-hour period |
| Objectives | Primary Endpoint: Following are based on evaluable subjects. Evaluable subjects are naïve with no preexposure to the virus and have not been vaccinated. All subjects will be included in the ITT or mITT population. 1) Reduction in RBD binding by subject's saliva by at least 20% at 30 minutes post administration of IMMUNIGY relative to pre-administration control in the evaluable population. Secondary Endpoints: 1) Reduction in RBD binding by subject's saliva by at least 15% at 60 minutes post administration of IMMUNIGY relative to pre-administration control in the evaluable population. 2) Reduction in RBD binding by subject's saliva by at least 10% at 120 minutes post administration of IMMUNIGY relative to pre-administration control in the evaluable population. Tertiary Endpoints: 1) Reduction in RBD binding by subject's saliva by at least 5% >3 hours post administration of IMMUNIGY relative to pre-administration control in the evaluable and ITT/mITT population. 2) Reduction in RBD binding by subject's saliva by at least 20% at 30 minutes post administration of IMMUNIGY relative to pre-administration control in the ITT/mITT population. |

| | Study Protocol |
|---|---|
| | 3) Reduction in RBD binding by subject's saliva by at least 15% at 60 minutes post administration of IMMUNIGY relative to pre-administration control in the ITT/mITT population.<br>4) Reduction in RBD binding by subject's saliva by at least 10% at 120 minutes post administration of IMMUNIGY relative to pre-administration control in the mITT population. |
| Study Design | Subject will sign consent to collect saliva samples at pre-specified periodic times.<br>The saliva samples will be used only to test in the neutralizing assay developed by Lat Sciences.<br>The samples may be stored indefinitely for future analyses using the neutralizing assay (interference of RBD-ACE binding) developed by Lay Sciences.<br>Subject's saliva at pre-administration will serve as the untreated control.<br>Subjects will be administered with 20 mL of IMMUNIGY-Vistop (1 gm) and will be instructed to swish the product in the mouth for a period of 1 minute and then swallowed. 30 minutes prior to the administration of IMMUNIGY-Vistop, the subject will rinse their mouth thrice with plain water and abstain from eating or drinking anything till IMMUNIGY-Vistop is administered<br>Periodically, at 30 minutes, 1 hour and 2 hours samples of saliva will be collected<br>If possible, an additional saliva sample will be collected at 3+ hours.<br>Technical personnel from Reagene will oversee the sample collection and administration of IMMUNIGY-Vistop.<br>The analyses will be ongoing as the data accrues, without incurring alpha penalty.<br>Interim analyses following 10 subjects are enrolled in the study will be assessed for futility of the study to determine if the study will continue or end. |
| Selection Criteria (inclusion/exclusion) | Inclusion criteria:<br>This is an all-comer study, will include naïve, vaccinated and SARS CoV-2 infected subjects<br>Exclusion criteria:<br>Saliva samples with high mucoid content<br>Colored saliva, such as those from betel leaf chewing or excessive use of tobacco. |
| Monitoring And Data Collection For Each Subject | Technical personnel from Reagene will oversee the sample collection and administration of IMMUNIGY-Vistop.<br>Patient history will be recorded by Reagene Personnel<br>Reagene will record any other observations such as, subjects washing their mouth or drinking beverages post administration of IMMUNIGY-Vistop and prior to sample collection.<br>Reagene will record desirability of the product such as, flavor, texture, after taste (lingering taste), discomfort etc.<br>Saliva samples at 30, 60, 120 minutes will be collected for analyses<br>Additionally, saliva sample at 3+ hours will also be collected for analyses.<br>Saliva samples may be stored for additional testing in the future for neutralizing antibodies.<br>Data will be collected from the assay tests of the saliva samples and will be recorded.<br>The data recording of the subjects will be anonymous; meaning each subject will be assigned an enrollment number sequentially, such as Subject 001, Subject 002 etc.<br>Any samples collected and stored will be destroyed within one year following its collection and will be recorded by Reagene.<br>The samples collected from subjects will not be used to assess for any other than as intended in this protocol, which is the determination of neutralizing antibodies against CoV-2 virus, which is a measure of RBD binding to ACE2. |

| Study Protocol | |
|---|---|
| Population | All comers<br>Ages 18+<br>May be amended to include 12+ ages as well |
| Planned Sample Size | Minimally 15 evaluable subjects<br>Maximally 100 ITT/mITT subjects |
| Data Analysis | For treatment differences chi-square or t tests will be used depending on the sample size for all of the following analyses.<br>1. Point analyses at specific times will be assessed<br>2. Magnitude changes relative to baseline will also be assessed<br>3. For continuous variables, area under the under the curve analyses will be used.<br>Primary, Secondary and Tertiary endpoints will include all of the above analyses.<br>Missing data will be imputed using a median of all evaluable assessments at each timepoint. |
| Safety | The formulation is based on nutraceutical guidance and the components are generally recognized as Safe (GRAS) |
| Efficacy/Benefit | Retention of neutralizing activity as specified in the endpoints above baseline is determined to be beneficial and considered to be an efficacious product. |

This clinical study was aborted after 4 persons were enrolled due to high COVID rates at the study sites and due to restrictions imposed by the local government. Preliminary results of the clinical study demonstrate that the antibodies are effective in oral mucosa following administration of the product. Although the study was aborted due to COVID restrictions, the initial results demonstrated that vaccinated, unvaccinated and infected persons who consumed IMMU-NIGY-Vistop had elevated levels of neutralizing activity in their saliva for at least 3 hours after consumption of the product.

Applicants designed a study to test the ability of anti-RBD IgY formulated as a drink to boost RBD-ACE2 neutralizing activity in saliva after a single oral rinse with a lychee flavored drink containing the anti-RBD IgY. To determine the increase in saliva neutralizing activity, we designed a simple protocol. Healthy volunteers were provided with 10 ml of drink containing 16.6 µg/ml of purified anti-RBD IgY as an oral rinse. The volunteers rinsed their oral cavity for 3 minutes and then spit out the rinse. Saliva samples were collected at zero time (basal sample before oral rinse) and at 30, 1 hour, 2 hours and 3 hours after the rinse and stored at 4° C. till the dot blot assay was performed. Just prior to use, the saliva was gently centrifuged at 5000 RPM for 2 minutes to settle any debris and the supernatant (10 µl) was used in the dot blot. Data are reported as increase in neutralizing activity over the basal levels.

Figure 8:
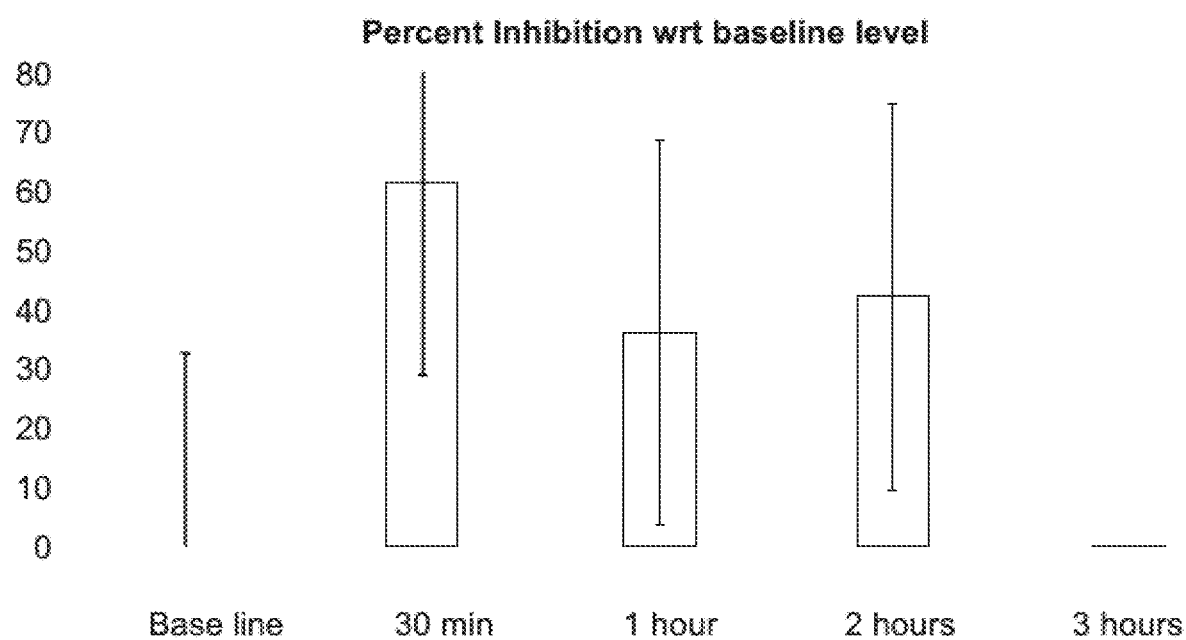
FIG. 8 shows the neutralizing activity of an oral rinse of an anti-RBD IgY antibody containing drink in a volunteer that received two shots of a SARS-CoV2 vaccine.
Figure 9:
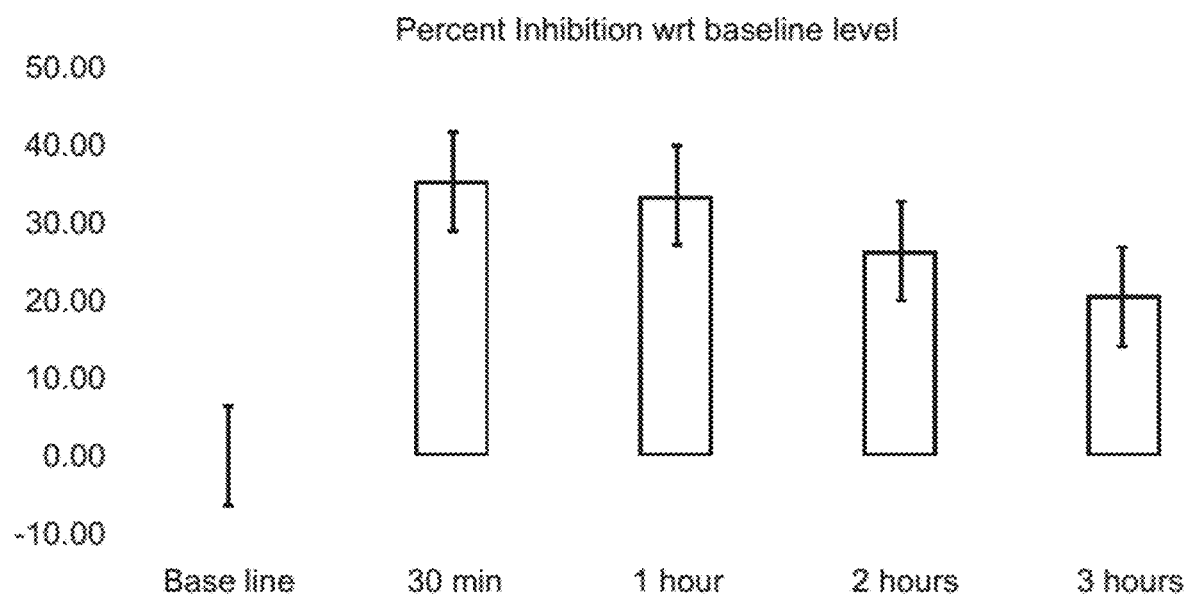
FIG. 9 shows the neutralization of the native (Wuhan) strain of the SARS-CoV2 virus by anti-RBD IgY antibody.
Figure 10:
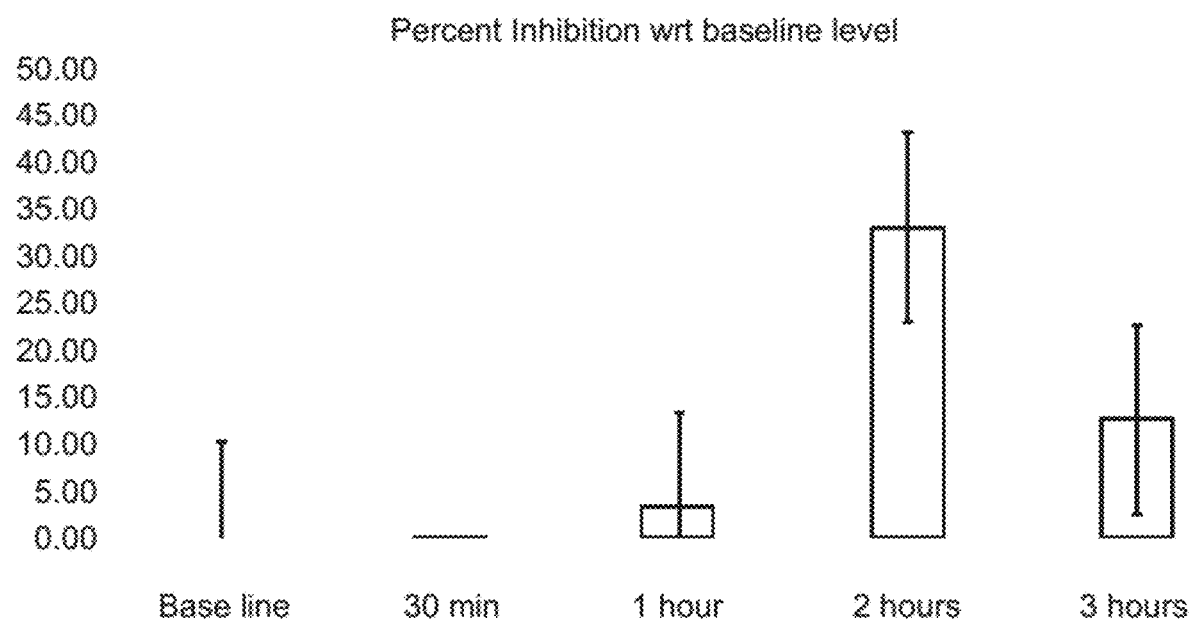
FIG. 10 shows the neutralization of the Delta strain of the SARS-CoV2 virus by anti-RBD IgY antibody.

FIG. 8 shows the neutralizing activity in saliva samples from a volunteer who was not vaccinated for SARS CoV2, and was RTPCR negative for SARS CoV2. The data show that there was a time-dependent increase in neutralizing activity of up to a 60% increase over baseline in this subject, with persistence of some activity 2 hours after oral rinse. FIG. 9 shows neutralizing activity in a volunteer who was vaccinated for SARS CoV2 one month prior to the study and did not have COVID 19. As shown in FIG. 9, there was up to a 30% increase in neutralizing activity above baseline and there was demonstrable activity even at 3 hours after the oral rinse. These data suggest that even in an individual who had one shot of a SARS CoV2 vaccine there was still an increase in neutralizing activity over base line. FIG. 10 shows neutralizing activity in another volunteer who had received two shots of a SARS CoV2 vaccine, with the second shot administered one month before the study. Interestingly, in this case the increase in saliva neutralizing activity was not detectable at 30 minutes but was clearly present at 1, 2 and 3 hours with peak activity of 30% increase at 2 hours (FIG. 10). This result suggests that even in fully vaccinated individuals, there is still an increase in saliva neutralizing activity by oral rinse with the IgY beverage. Finally the impact of oral rinse on an individual who had recently recovered from COVID 19 and was RTPCR negative for the virus at the time of this study was examined. There was no increase in the neutralizing activity at any time point after the oral rinse. It is possible that the lack of increase in neutralizing activity was due to high levels of neutralizing activity in this individual with recent COVID 19 infection, but that remains to be tested.

The invention claimed is:

1. A hyperimmunized egg produced by an animal that has been hyperimmunized with an antigen consisting of the amino acid sequence of SEQ ID NO: 19, wherein the level of antibodies to the antigen in the hyperimmunized egg is increased relative to an egg from an animal that has not been hyperimmunized.

2. The hyperimmunized egg of claim 1, wherein the antibodies in the hyperimmunized egg have a titer of at least 80,000 as measured by optical density.

3. A hyperimmunized egg product obtained from the hyperimmunized egg of claim 1, wherein the hyperimmunized egg product is whole egg, egg yolk, or the purified or partially purified IgY antibody fraction to SARS-COV-2 from the hyperimmunized egg.

4. A pharmaceutical composition comprising the hyperimmunized egg product of claim 3 and a pharmaceutically acceptable carrier.

5. The pharmaceutical composition of claim 4 formulated for oral, nasal or ocular administration.

6. The pharmaceutical composition of claim 5, wherein:

the pharmaceutical composition is formulated for administration to the subject as an oral rinse, by inhalation, by nasal drops or by eye drops; or the pharmaceutical composition is a liquid, a freeze-dried powder, or formulated to be administered as a spray.

7. The pharmaceutical composition of claim 4, wherein the pharmaceutically acceptable carrier comprises a compound that is generally recognized as safe (GRAS) and an excipient that increases solubility, stability and/or dissolution of the pharmaceutical composition relative to the pharmaceutical composition lacking the compound.

8. The pharmaceutical composition of claim 6, wherein the hyperimmunized egg product is formulated in nanoparticles or in an emulsion.

9. The hyperimmunized egg product of claim 3, wherein the hyperimmunized egg product is in a form of nanoparticles having a diameter less than 1000 nm.

10. The hyperimmunized egg product of claim 3, wherein the hyperimmunized egg product is in a form of microparticles having a diameter in the range of about 0.1 to 10 microns.

11. The hyperimmunized egg product of claim 3, wherein the hyperimmunized egg product is in a form of microparticles having a diameter in the range of about 10 to 100 microns.

12. The hyperimmunized egg product of claim 3, wherein the hyperimmunized egg product is encapsulated in an encapsulating material.

13. The hyperimmunized egg product of claim 3, wherein the hyperimmunized egg product is mixed with an agent that increases flow properties of the hyperimmunized egg product relative to the hyperimmunized egg product lacking the agent.

14. The hyperimmunized egg product of claim 3, wherein the hyperimmunized egg product is in a form of nanoparticles having a diameter in the range of about 10 to 1000 nm.

* * * * *

SEQUENCE LISTING

```
Sequence total quantity: 19
SEQ ID NO: 1           moltype = AA  length = 1273
FEATURE                Location/Qualifiers
source                 1..1273
                       mol_type = protein
                       organism = SarsCoV2 virus
SEQUENCE: 1
MFVFLVLLPL VSSQCVNLTT RTQLPPAYTN SFTRGVYYPD KVFRSSVLHS TQDLFLPFFS   60
NVTWFHAIHV SGTNGTKRFD NPVLPFNDGV YFASTEKSNI IRGWIFGTTL DSKTQSLLIV  120
NNATNVVIKV CEFQFCNDPF LGVYYHKNNK SWMESEFRVY SSANNCTFEY VSQPFLMDLE  180
GKQGNFKNLR EFVFKNIDGY FKIYSKHTPI NLVRDLPQGF SALEPLVDLP IGINITRFQT  240
```

```
                        -continued
LLALHRSYLT PGDSSSGWTA GAAAYYVGYL QPRTFLLKYN ENGTITDAVD CALDPLSETK    300
CTLKSFTVEK GIYQTSNFRV QPTESIVRFP NITNLCPFGE VFNATRFASV YAWNRKRISN    360
CVADYSVLYN SASFSTFKCY GVSPTKLNDL CFTNVYADSF VIRGDEVRQI APGQTGKIAD    420
YNYKLPDDFT GCVIAWNSNN LDSKVGGNYN YLYRLFRKSN LKPFERDIST EIYQAGSTPC    480
NGVEGFNCYF PLQSYGFQPT NGVGYQPYRV VVLSFELLHA PATVCGPKKS TNLVKNKCVN    540
FNFNGLTGTG VLTESNKKFL PFQQFGRDIA DTTDAVRDPQ TLEILDITPC SFGGVSVITP    600
GTNTSNQVAV LYQDVNCTEV PVAIHADQLT PTWRVYSTGS NVFQTRAGCL IGAEHVNNSY    660
ECDIPIGAGI CASYQTQTNS PRRARSVASQ SIIAYTMSLG AENSVAYSNN SIAIPTNFTI    720
SVTTEILPVS MTKTSVDCTM YICGDSTECS NLLLQYGSFC TQLNRALTGI AVEQDKNTQE    780
VFAQVKQIYK TPPIKDFGGF NFSQILPDPS KPSKRSFIED LLFNKVTLAD AGFIKQYGDC    840
LGDIAARDLI CAQKFNGLTV LPPLLTDEMI AQYTSALLAG TITSGWTFGA GAALQIPFAM    900
QMAYRFNGIG VTQNVLYENQ KLIANQFNSA IGKIQDSLSS TASALGKLQD VVNQNAQALN    960
TLVKQLSSNF GAISSVLNDI LSRLDKVEAE VQIDRLITGR LQSLQTYVTQ QLIRAAEIRA   1020
SANLAATKMS ECVLGQSKRV DFCGKGYHLM SFPQSAPHGV VFLHVTYVPA QEKNFTTAPA   1080
ICHDGKAHFP REGVFVSNGT HWFVTQRNFY EPQIITTDNT FVSGNCDVVI GIVNNTVYDP   1140
LQPELDSFKE ELDKYFKNHT SPDVDLGDIS GINASVVNIQ KEIDRLNEVA KNLNESLIDL   1200
QELGKYEQYI KWPWYIWLGF IAGLIAIVMV TIMLCCMTSC CSCLKGCCSC GSCCKFDEDD   1260
SEPVLKGVKL HYT                                                     1273

SEQ ID NO: 2              moltype = AA   length = 960
FEATURE                   Location/Qualifiers
source                    1..960
                          mol_type = protein
                          organism = SarsCoV virus
SEQUENCE: 2
MPIFLLFLTL TSGSDLDRCT TFDDVQAPNY TQHTSSMRGV YYPDEIFRSD TLYLTQDLFL     60
PFYSNVTGFH TINHTFGNPV IPFKDGIYFA ATEKSNVVRG WVFGSTMNNK SQSVIIINNS    120
TNVVIRACNF ELCDNPFFAV SKPMGTQTHT MIFDNAFNCT FEYISDAFSL DVSEKSGNFK    180
HLREFVFKNK DGFLYVYKGY QPIDVVRDLP SGFNTLKPIF KLPLGINITN FRAILTAFSP    240
AQDIWGTSAA AYFVGYLKPT TFMLKYDENG TITDAVDCSQ NPLAELKCSV KSFEIDKGIY    300
QTSNFRVVPS GDVVRFPNIT NLCPFGEVFN ATKFPSVYAW ERKKISNCVA DYSVLYNSTF    360
FSTFKCYGVS ATKLNDLCFS NVYADSFVVK GDDVRQIAPG QTGVIADYNY KLPDDFMGCV    420
LAWNTRNIDA TSTGNYNYKY RYLRHGKLRP FERDISNVPF SPDGKPCTPP ALNCYWPLND    480
YGFYTTTGIG YQPYRVVVLS FELLNAPATV CGPKLSTDLI KNQCVNFNFN GLTGTGVLTP    540
SSKRFQPFQQ FGRDVSDFTD SVRDPKTSEI LDISPCSFGG VSVITPGTNA SSEVAVLYQD    600
VNCTDVSTAI HADQLTPAWR IYSTGNNVFQ TQAGCLIGAE HVDTSYECDI PIGAGICASY    660
HTVSLLRSTS QKSIVAYTMS LGADSSIAYS NNTIAIPTNF SISITTEVMP VSMAKTSVDC    720
NMYICGDSTE CANLLLQYGS FCTQLNRALS GIAAEQDRNT REVFAQVKQM YKTPTLKYFG    780
GFNFSQILPD PLKPTKRSFI EDLLFNKVTL ADAGFMKQYG ECLGDINARD LICAQKFNGL    840
TVLPPLLTDD MIAAYTAALV SGTATAGWTF GAGAALQIPF AMQMAYRFNG IGVTQNVLYE    900
NQKQIANQFN KAISQIQESL TTTSTALGKL QDVVNQNAQA LNTLVKQLSS NFGAISSVLN    960

SEQ ID NO: 3              moltype = AA   length = 1353
FEATURE                   Location/Qualifiers
source                    1..1353
                          mol_type = protein
                          organism = MERS virus
SEQUENCE: 3
MIHSVFLLMF LLTPTESYVD VGPDSVKSAC IEVDIQQTFF DKTWPRPIDV SKADGIIYPQ     60
GRTYSNITIT YQGLFPYQGD HGDMYVYSAG HATGTTPQKL FVANYSQDVK QFANGFVVRI    120
GAAANSTGTV IISPSTSATI RKIYPAFMLG SSVGNFSDGK MGRFFNHTLV LLPDGCGTLL    180
RAFYCILEPR SGNHCPAGNS YTSFATYHTP ATDCSDGNYN RNASLNSFKE YFNLRNCTFM    240
YTYNITEDEI LEWFGITQTA QGVHLFSSRY VDLYGGNMFQ FATLPVYDTI KYYSIIPHSI    300
RSIQSDRKAW AAFYVYKLQP LTFLLDFSVD GYIRRAIDCG FNDLSQLHCS YESFDVESGV    360
YSVSSFEAKP SGSVVEQAEG VECDFSPLLS GTPPQVYNFK RLVFTNCNYN LTKLLSLFSV    420
NDFTCSQISP AAIASNCYSS LILDYFSYPL SMKSDLSVSS AGPISQFNYK QSFSNPTCLI    480
LATVPHNLTT ITKPLKYSYI NKCSRFLSDD RTEVPQLVNA NQYSPCVSIV PSTVWEDGDY    540
YRKQLSPLEG GGWLVASGST VAMTEQLQMG FGITVQYGTD TNSVCPKLEF ANDTKIASQL    600
GNCVEYSLYG VSGRGVFQNC TAVGVRQQRF VYDAYQNLVG YSDDGNYYC LRACVSVPVS    660
VIYDKETKTH ATLFGSVACE HISSTMSQYS RSTRSMLKRR DSTYGPLQTP VGCVLGLVNS    720
SLFVEDCKLP LGQSLCALPD TPSTLTPRSV RSVPGEMRLA SIAFNHPIQV DQLNSSYFKL    780
SIPTNFSFGV TQEYIQTTIQ KVTVDCKQYV CNGFQKCEQL LREYGQFCSK INQALHGANL    840
RQDDSVRNLF ASVKSSQSSP IIPGFGGDFN LTLLEPVSIS TGSRSARSAI EDLLFDKVTI    900
ADPGYMQGYD DCMQQGPASA RDLICAQYVA GYKVLPPLMD VNMEAAYTSS LLGSIAGVGW    960
TAGLSSFAAI PFAQSIFYRL NGVGITQQVL SENQKLIANK FNQALGAMQT GFTTTNEAFH   1020
KVQDAVNNNA QALSKLASEL SNTFGAISAS IGDIIQRLDV LEQDAQIDRL INGRLTTLNA   1080
FVAQQLVRSE SAALSAQLAK DKVNECVKAQ SKRSGFCGQG THIVSFVVNA PNGLYFMHVG   1140
YYPSNHIEVV SAYGLCDAAN PTNCIAPVNG YFIKTNNTRI VDEWSYTGSS FYAPEPITSL   1200
NTKYVAPQVT YQNISTNLPP PLLGNSTGID FQDELDEFFK NVSTSIPNFG SLTQINTTLL   1260
DLTYEMLSLQ QVVKALNESY IDLKELGNYT YYNKWPWYIW LGFIAGLVAL ALCVFFILCC   1320
TGCGTNCMGK LKCNRCCDRY EEYDLEPHKV HVH                               1353

SEQ ID NO: 4              moltype = AA   length = 1351
FEATURE                   Location/Qualifiers
source                    1..1351
                          mol_type = protein
                          organism = HKU1 virus
SEQUENCE: 4
MFLIIFILPT TLAVIGDFNC TNSFINDYNK TIPRISEDVV DVSLGLGTYY VLNRVYLNTT     60
```

```
LLFTGYFPKS GANFRDLALK GSIYLSTLWY KPPPFLSDFNN GIFSKVKNTK LYVNNTLYSE    120
FSTIVIGSVF VNTSYTIVVQ PHNGILEITA CQYTMCEYPH TVCKSKGSIR NESWHIDSSE    180
PLCLFKKNFT YNVSADWLYF HFYQERGVFY AYYADVGMPT TPFLFSLYLGT ILSHYYVMPL   240
TCNAISSNTD NETLEYWVTP LSRRQYLLNF DEHGVITNAV DCSSSFLSEI QCKTQSFAPN    300
TGVYDLSGFT VKPVATVYRR IPNLPDCDID NWLNNVSVPS PLNWERRIFS NCNFNLSTLL    360
RLVHVDSFSC NNLDKSKIFG SCFNSITVDK FAIPNRRRDD LQLGSSGFLQ SSNYKIDISS    420
SSCQLYYSLP LVNVTINNFN PSSWNRRYGF GSFNVSSYDV VYSDHCFSVN SDFCPCADRS    480
VVNSCVKSKP PSAICPAGTK YRHCDLDTTL YVKNWCRCSC LPDPISTYSP NTCPQKKVVV    540
GIGEHCPGLG INEEKCGTQL NHSSCSCSPD AFLGWSFDSC ISNNRCNIFS NPIFNGINSG    600
TTCSNDLLYS NTEVSTGCV NYDLYGITGQ GIFKEVSAAY YNNWQNLLYD SNGNIIGFKD    660
FLTNKTYTIL PCYSGRVSAA FYQNSSSPAL LYRNLKCSYV LNNISFISQP FYFDSYLGCV    720
LNAVNLTSYS VSSCDLRMGS GFCIDYALPS SRRKRRGISS PYRFVTFEPF NVSFVNDSVE    780
TVGGLFEIQI PTNFTIAGHE EFIQTSSPKV TIDCSAFVCS NYAACHDLLS EYGTFCDNIN    840
SILNEVNDLL DITQLQVANA LMQGVTLSSN LNTNLHSDVD NIDFKSLLGC LGSQCGSSSR    900
SLLEDLLFNK VKLSDVGFVE AYNNCTGGSE IRDLLCVQSF NGIKVLPPIL SETQISGYTT    960
AATVAAMFPP WSAAAGVPFS LNVQYRINGL GVTMDVLNKN QKLIANAFNK ALLSIQNGFT   1020
ATNSALAKIQ SVVNANAQAL NSLLQQLFNK FGAISSSLQE ILSRLDNLEA QVQIDRLING   1080
RLTALNAYVS QQLSDITLIK AGASRAIEKV NECVKSQSPR INFCGNGNHI LSLVQNAPYG   1140
LLFIHFSYKP TSFKTVLVSP GLCLSGDRGI APKQGYFIKQ NDSWMFTGSS YYYPEPISDK   1200
NVVFMNSCSV NFTKAPFIYL NNSIPNLSDF EAEFSLWFKN HTSIAPNLTF NSHINATFLD   1260
LYYEMNVIQE SIKSLNSSFI NLKEIGTYEM YVKWPWYIWL LIVILFIIFL MILFFICCCT   1320
GCGSACFSKC HNCCDEYGGH NDFVIKASHD D                                  1351

SEQ ID NO: 5           moltype = AA  length = 1356
FEATURE                Location/Qualifiers
source                 1..1356
                       mol_type = protein
                       organism = NL63 virus
SEQUENCE: 5
MKLFLILLVL PLASCFFTCN SNANLSMLQL GVPDNSSTIV TGLLPTHWFC ANQSTSVYSA     60
NGFFYIDVGN HRSAFALHTG YYDANQYYIY VTNEIGLNAS VTLKICKFSR NTTFDFLSNA    120
SSSFDCIVNL LFTEQLGAPL GITISGETVR LHLYNVTRTF YVPAAYKLTK LSVKCYFNYS    180
CVFSVVNATV TVNVTTHNGR VVNYTVCDDC NGYTDNIFSV QQDGRIPNGF PFNNWFLLTN    240
GSTLVDGVSR LYQPLRLTCL WPVPGLKSST GFVYFNATGS DVNCNGYQHN SVVDVMRYNL    300
NFSANSLDNL KSGVIVFKTL QYDVLFYCSN SSSGVLDTTI PFGPSSQPYY CFINSTINTT    360
HVSTFVGILP PTVREIVVAR TGQFYINGPK YFDLGFIEAV NFNVTTASAT DPFWTVAFATF   420
VDVLVNVSAT NIQNLLYCDS PFEKLQCEHL QFGLQDGFYS ANFLDDNVLP ETYVALPIYY    480
QHTDINFTAT ASFGGSCYVC KPHQVNISLN GNTSVCVRTS HFSIRYIYNR VKSGSPGDSS    540
WHIYLKSGTC PFSFSKLNNF QKFKTICFST VEVPGSCNFP LEATWHYTSY TIVGALYVTW    600
SEGNSITGVP YPVSGIREFS NLVLNNCTKY NIYDYVGTGI IRSSNQSLAG GITYVSNSGN    660
LLGFKNVSTG NIFIVTPCNQ PDQVAVYQQS IIGAMTAVNE SRYGLQNLLQ LPNFYYVSNG    720
GNNCTTAVMT YSNFGICADG SLIPVRPRTS SDNGISAIII ANLSIPSNWT TSVQVEYLQI    780
TSTPIVVDCA TYVCNGNPRC KNLLKQYTSA CKTIEDALRL SAHLETNDVS SMLTFDSNAF    840
SLANVTSFGD YNLSSVLPQR NIRSSRIAGR SALEDLLFSK VVTSGLGTVD VDYKSCTKGL    900
SIADLACAQY YNGIMVLPGV ADAERMAMYT GSLIGGMVLG GLTSAAAIPF SLALQARLNY    960
VALQTDVLQE NQKILAASFN KAINNIVASF SSVNDAITQT AEAIHTVTIA LNKIQDVVNQ   1020
QGSALNHLTS QLRHNFQAIS NSIQAIYDRL DSIQADQYQP RLITGRLAAL NAFVSQVLNK   1080
YTEVRGSRRL AQQKINECVK SQSNRYGFCG NGTHIFSIVN SAPDGLLFLH TVLLPTDYKN   1140
VKAWSGICVD GIYGYVLRQP NLVLYSDNGV FRVTSRVMFQ PRLPVLSDFV QIYNCNVTFV   1200
NISRVELHTV IPDYVDVNKT LQEFAQNLPK YVKPNFDLTP FNLTYLNLSS ELKQLEAKTA   1260
SLFQTTVELQ GLIDQINSTY VDLKLLNRFE NYIKWPWWVW LIISVFVVVL LSLLVFCCLS   1320
TGCCGCCNCL TSSMRGCCDC GSTKLPYYEF EKVHVQ                             1356

SEQ ID NO: 6           moltype = AA  length = 1353
FEATURE                Location/Qualifiers
source                 1..1353
                       mol_type = protein
                       organism = OC43 virus
SEQUENCE: 6
MFLILLISLP TAFAVIGDLK CTSDNINDKD TGPPPISTDT VDVTNGLGTY YVLDRVYLNT     60
TLFLNGYYPT SGSTYRNMAL KGSVLLSRLW FKPPFLSDFI NGIFAKVKNT KVIKDRVMYS    120
EFPAITIGST FVNTSYSVVV QPRTINSTQD GDNKLQGLLE VSVCQYNMCE YPQTICHPNL    180
GNHRKELWHL DTGVVSCLYK RNFTYDVNAD YLYFHFYQEG GTFYAYFTDT GVVTKFLFNV    240
YLGMALSHYY VMPLTCNSKL TLEYWVTPLT SRQYLLAFNQ DGIIFNAEDC MSDFMSEIKC    300
KTQSIAPPTG VYELNGYTVQ PIADVYRRKP NLPNCNIEAW LNDKSVPSPL NWERKTFSNC    360
NFNMSSLMSF IQADSFTCNN IDAAKIYGMC FSSITIDKFA IPNGRKVDLQ LGNLGYLQSF    420
NYRIDTTATS CQLYYNLPAA NVSVSRFNPS TWNKRFGFIE DSVFKPRPAG VLTNHDVVYA    480
QHCFKAPKNF CPCKLNGSCV GSGPGKNNGI GTCPAGTNYL TCDNLCTPDP ITFTGTYKCP    540
QTKSLVGIGE HCSGLAVKSD YCGGNSCTCR PQAFLGWSAD SCLQGDKCNI FANFILHDVN    600
SGLTCSTDLQ KANTDIILGV CVNYDLYGIL GQGIFVEVNA TYYNSWQNLL YDSNGNLYGF    660
RDYIINRTFM IRSCYSGRVS AAFHANSSEP ALLFRNIKCN YVFNNSLTRQ LQPINYFDSY    720
LGCVVNAYNS TAISVQTCDL TVGSGYCVDY SKNRRSRGAI TTGYRFTNFE PFTVNSVNDS    780
LEPVGGLYEI QIPSEFTIGN MVEFIQTSSP KVTIDCAAFV CGDYAACKSQ LVEYGSFCDN    840
INAILTEVNE LLDTTQLQVA NSLMNGVTLS TKLKDGVNFN VDDINFSPVL GCLGSECSKA    900
SSRSAIEDLL FDKVKLSDVG FVEAYNNCTG GAEIRDLICV QSYKGIKVLP PLLSENQISG    960
YTLAATSASL PPPWTAAAGV PFYLNVQYRI NGLGVTMDVL SQNQKLIANA FNNALYAIQE   1020
GFDATNSALV KIQAVVNANA EALNNLLQQL SNRFGAISAS LQEILSRLDA LEAEAQIDRL   1080
INGRLTALNA YVSQQLSDST LVKFSAAQAM EKVNECVKSQ SSRINFCGNG NHIISLVQNA   1140
PYGLYFIHFS YVPTKYVTAR VSPGLCIAGD RGIAPKSGYF VNVNNTWMYT GSGYYYPEPI   1200
```

```
                                     -continued
TENNVVVMST CAVNYTKAPY VMLNTSIPNL PDFKEELDQW FKNQTSVAPD LSLDYINVTF  1260
LDLQVEMNRL QEAIKVLNQS YINLKDIGTY EYYVKWPWYV WLLICLAGVA MLVLLFFICC  1320
CTGCGTSCFK KCGGCCDDYT GYQELVIKTS HDD                              1353

SEQ ID NO: 7               moltype = AA   length = 1173
FEATURE                    Location/Qualifiers
source                     1..1173
                           mol_type = protein
                           organism = 229E virus
SEQUENCE: 7
MFVLLVAYAL LHIAGCQTTN GLNTSYSVCN GCVGYSENVF AVESGGYIPS DFAFNNWFLL   60
TNTSSVVDGV VRSFQPLLLN CLWSVSGLRF TTGFVYFNGT GRGDCKGFSS DVLSDVIRYN  120
LNFEENLRRG TILFKTSYGV VVFYCTNNTL VSGDAHIPFG TVLGNFYCFV NTTIGNETTS  180
AFVGALPKTV REFVISRTGH FYINGYRYFT LGNVEAVNFN VTTAETTDFC TVALASYADV  240
LVNVSQTSIA NIIYCNSVIN RLRCDQLSFD VPDGFYSTSP IQSVELPVSI VSLPVYHKHT  300
FIVLYVDFKP QSGGGKCFNC YPAGVNITLA NFNETKGPLC VDTSHFTTKY VAVYANVGRW  360
SASINTGNCP FSFGKVNNFV KFGSVCFSLK DIPGGCAMPI VANWAYSKYY TIGSLYVSWS  420
DGDGITGVPQ PVEGVSSFMN VTLDKCTKYN IYDVSGVGVI RVSNDTFLNG ITYTSTSGNL  480
LGFKDVTKGT IYSITPCNPP DQLVVYQQAV VGAMLSENFT SYGFSNVVEL PKFFYASNGT  540
YNCTDAVLTY SSFGVCADGS IIAVQPRNVS YDSVSAIVTA NLSIPSNWTT SVQVEYLQIT  600
STPIVVDCST YVCNGNVRCV ELLKQYTSAC KTIEDALRNS ARLESADVSE MLTFDKKAFT  660
LANVSSFGDY NLSSVIPSLP TSGSRVAGRS AIEDILFSKL VTSGLGTVDA DYKKCTKGLS  720
IADLACAQYY NGIMVLPGVA DAERMAMYTG SLIGGIALGG LTSAVSIPFS LAIQARLNYV  780
ALQTDVLQEN QKILAASFNK AMTNIVDAFT GVNDAITQTS QALQTVATAL NKIQDVVNQQ  840
GNSLNHLTSQ LRQNFQAISS SIQAIYDRLD TIQADQQVDR LITGRLAALN VFVSHTLTKY  900
TEVRASRQLA QQKVNECVKS QSKRYGFCGN GTHIFSVNA GLRVFLHT VLLPTQYKDV   960
EAWSGLCVDG TNGYVLRQPN LALYKEGNYY RITSRIMFEP RIPTMADFVQ IENCNVTFVN 1020
ISRSELQTIV PEYIDVNKTL QELSYKLPNY TVPDLVVEQY NQTILNLTSE ISTLENKSAE 1080
LNYTVQKLQT LIDNINSTLV DLKWLNRVET YIKWPWWVWL CISVVLIFVV SMLLLCCCST 1140
GCCGFFSCFA SSIRGCCEST KLPYYDVEKI HIQ                             1173

SEQ ID NO: 8               moltype = AA   length = 419
FEATURE                    Location/Qualifiers
source                     1..419
                           mol_type = protein
                           organism = SARSCoV2 virus
SEQUENCE: 8
MSDNGPQNQR NAPRITFGGP SDSTGSNQNG ERSGARSKQR RPQGLPNNTA SWFTALTQHG   60
KEDLKFPRGQ GVPINTNSSP DDQIGYYRRA TRRIRGGDGK MKDLSPRWYF YYLGTGPEAG  120
LPYGANKDGI IWVATEGALN TPKDHIGTRN PANNAAIVLQ LPQGTTLPKG FYAEGSRGGS  180
QASSRSSSRS RNSSRNSTPG SSRGTSPARM AGNGGDAALA LLLLDRLNQL ESKMSGKGQQ  240
QQGQTVTKKS AAEASKKPRQ KRTATKAYNV TQAFGRRGPE QTQGNFGDQE LIRQGTDYKH  300
WPQIAQFAPS ASAFFGMSRI GMEVTPSGTW LTYTGAIKLD DKDPNFKDQV ILLNKHIDAY  360
KTFPPTEPKK DKKKKADETQ ALPQRQKKQQ TVTLLPAADL DDFSKQLQQS MSSADSTQA   419

SEQ ID NO: 9               moltype = AA   length = 422
FEATURE                    Location/Qualifiers
source                     1..422
                           mol_type = protein
                           organism = SARSCoV virus
SEQUENCE: 9
MSDNGPQSNQ RSAPRITFGG PTDSTDNNQN GGRNGARPKQ RRPQGLPNNT ASWFTALTQH   60
GKEELRFPRG QGVPINTNSG PDDQIGYYRR ATRRVRGGDG KMKELSPRWY FYYLGTGPEA  120
SLPYGANKEG IWVATEGAL NTPKDHIGTR NPNNNAATVL QLPQGTTLPK GFYAEGSRGG  180
SQASSRSSSR SRGNSRNSTP GSSRGNSPAR MASGGGETAL ALLLLDRLNQ LESKVSGKGQ  240
QQQGQTVTKK SAAEASKKPR QKRTATKQYN VTQAFGRRGP EQTQGNFGDQ DLIRQGTDYK  300
HWPQIAQFAP SASAFFGMSR IGMEVTPSGT WLTYHGAIKL DDKDPQFKDN VILLNKHIDA  360
YKTFPPTEPK DKKKKTDEA QPLPQRQKKQ PTVTLLPAAD MDDFSRQLQN SMSGASADST  420
QA                                                                422

SEQ ID NO: 10              moltype = AA   length = 413
FEATURE                    Location/Qualifiers
source                     1..413
                           mol_type = protein
                           organism = MERS virus
SEQUENCE: 10
MASPAAPRAV SFADNNDITN TNLSRGRGRN PKPRAAPNNT VSWYTGLTQH GKVPLTFPPG   60
QGVPLNANST PAQNAGYWRR QDRKINTGNG IKQLAPRWYF YYTGTGPEAA LPFRAVKDGI  120
VWVHEDGATD APSTFGTRNP NNDSAIVTQF APGTKLPKNF HIEGTGGNSQ SSSRASSVSR  180
NSSRSSSQGS RSGNSTRGTS PGPSGIGAVG GDLLYLDLLN RLQALESGKV KQSQPKVITK  240
KDAAAAKNKM RHKRTSTKSF NMVQAFGLRK PGDLQGNFGD LQLNKLGTED PRWPQIAELA  300
PTASAFMGMS QFKLTHQNND DHGNPVYFLR YSGAIKLDPK NPNYNKWLEL LEQNIDAYKT  360
FPKKEKKQKA PKEESTDQMS EPPKEQRVQG SITQRTRTRP SVQPGPMIDV NTD         413

SEQ ID NO: 11              moltype = AA   length = 441
FEATURE                    Location/Qualifiers
source                     1..441
                           mol_type = protein
                           organism = HKU1 virus
```

```
SEQUENCE: 11
MSYTPGHYAG SRSSSGNRSG ILKKTSWADQ SERNYQTFNR GRKTQPKFTV STQPQGNTIP     60
HYSWFSGITQ FQKGRDFKFS DGQGVPIAFG VPPSEAKGYW YRHSRRSFKT ADGQQKQLLP    120
RWYFYYLGTG PYANASYGES LEGVFWVANH QADTSTPSDV SSRDPTTQEA IPTRFPPGTI    180
LPQGYYVEGS GRSASNSRPG SRSQSRGPNN RSLSRSNSNF RHSDSIVKPD MADEIANLVL    240
AKLGKDSKPQ QVTKQNAKEI RHKILTKPRQ KRTPNKHCNV QQCFGKRGPS QNFGNAEMLK    300
LGTNDPQFPI LAELAPTPGA FFFGSKLDLV KRDSEADSPV KDVFELHYSG SIRFDSTLPG    360
FETIMKVLEE NLNAYVNSNQ NTDSDSLSSK PQRKRGVKQL PEQFDSLNLS AGTQHISNDF    420
TPEDHSLLAT LDDPYVEDSV A                                              441

SEQ ID NO: 12           moltype = AA  length = 377
FEATURE                 Location/Qualifiers
source                  1..377
                        mol_type = protein
                        organism = NL63 virus
SEQUENCE: 12
MASVNWADDR AARKKFPPPS FYMPLLVSSD KAPYRVIPRN LVPIGKGNKD EQIGYWNVQE     60
RWRMRRGQRV DLPPKVHFYY LGTGPHKDLK FRQRSDGVVW VAKEGAKTVN TSLGNRKRNQ    120
KPLEPKFSIA LPPELSVVEF EDRSNNSSRA SSRSSTRNNS RDSSRSTSRQ QSRTRSDSNQ    180
SSSSDLVAAVT LALKNLGFDN QSKSPSSSGT STPKKPNKPL SQPRADKPSQ LKKPRWKRVP   240
TREENVIQCF GPRDFNHNMG DSDLVQNGVD AKGFPQLAEL IPNQAALFFD SEVSTDEVGD    300
NVQITYTYKM LVAKDNKNLP KFIEQISAFT KPSSIKEMQS QSSHVAQNTV LNASIPESKP    360
LADDDSAIIE IVNEVLH                                                   377

SEQ ID NO: 13           moltype = AA  length = 448
FEATURE                 Location/Qualifiers
source                  1..448
                        mol_type = protein
                        organism = OC43 virus
SEQUENCE: 13
MSFTPGKQSS SRASSGNRSG NGILKWADQS DQVRNVQTRG RRAQPKQTAT SQQPSGGNVV     60
PYYSWFSGIT QFQKGKEFEF VEGQGPPIAP GVPATEAKGY WYRHNRGSFK TADGNQRQLL    120
PRWYFYYLGT GPHAKDQYGT DIDGVYWVAS NQADVNTPAD IVDRDPSSDE AIPTRFPPGT    180
VLPQGYYIEG SGRSAPNSRS TSRTSSRASS AGSRSRANSG NRTPTSGVTP DMADQIASLV    240
LAKLGKDATK PQQVTKHTAK EVRQKILNKP RQKRSPNKQC TVQQCFGKRG PNQNFGGGEM    300
LKLGTSDPQF PILAELAPTA GAFFFGSRLE LAKVQNLSGN PDEPQKDVYE LRYNGAIRFD    360
STLSGFETIM KVLNENLNAY QQQDGMMNMS PKPQRQRGHK NGQGENDNIS VAVPKSRVQQ    420
NKSRELTAED ISLLKKMDEP YTEDTSEI                                       448

SEQ ID NO: 14           moltype = AA  length = 389
FEATURE                 Location/Qualifiers
source                  1..389
                        mol_type = protein
                        organism = 229E virus
SEQUENCE: 14
MATVKWADAS EPQRGRQGRI PYSLYSPLLV DSEQPWKVIP RNLVPINKKD KNKLIGYWNV     60
QKRFRTRKGK RVDLSPKLHF YYLGTGPHKD AKFRERVEGV VWVAVDGAKT EPTGYGVRRK    120
NSEPEIPHFN QKLPNGVTVV EEPDSRAPSR SQSRSQSRGR GESKPQSRNP SSDRNHNSQD    180
DIMKAVAAAL KSLGFDKPQE KDKKSAKTGT PKPSRNQSPA SSQTSAKSLA RSQSSETKEQ    240
KHEMQKPRWK RQPNDDVTSN VTQCFGPRDL DHNFGSAGVV ANGVKAKGYP QFAELVPSTA    300
AMLFDSHIVS KESGNTVVLT FTTRVTVPKD HPHLGKFLEE LNAFTREMQQ HPLLNPSALE    360
FNPSQTSPAT AEPVRDEVSI ETDIIDEVN                                      389

SEQ ID NO: 15           moltype = AA  length = 805
FEATURE                 Location/Qualifiers
source                  1..805
                        mol_type = protein
                        organism = Homo sapiens
SEQUENCE: 15
MSSSSWLLLS LVAVTAAQST IEEQAKTFLD KFNHEAEDLF YQSSLASWNY NTNITEENVQ     60
NMNNAGDKWS AFLKEQSTLA QMYPLQEIQN LTVKLQLQAL QQNGSSVLSE DKSKRLNTIL    120
NTMSTIYSTG KVCNPDNPQE CLLLEPGLNE IMANSLDYNE RLWAWESWRS EVGKQLRPLY    180
EEYVVLKNEM ARANHYEDYG DYWRGDYEVN GVDGYDYSRG QLIEDVEHTF EEIKPLYEHL    240
HAYVRAKLMN AYPSYISPIG CLPAHLLGDM WGRFWTNLYS LTVPFGQKPN IDVTDAMVDQ    300
AWDAQRIFKE AEKFFVSVGL PNMTQGFWEN SMLTDPGNVQ KAVCHPTAWD LGKGDFRILM    360
CTKVTMDDFL TAHHEMGHIQ YDMAYAAQPF LLRNGANEGF HEAVGEIMSL SAATPKHLKS    420
IGLLSPDFQE DNETEINFLL KQALTIVGTL PFTYMLEKWR WMVFKGEIPK DQWMKKWWEM    480
KREIVGVVEP VPHDETYCDP ASLFHVSNDY SFIRYYTRTL YQFQFQEALC QAAKHEGPLH    540
KCDISNSTEA GQKLFNMLRL GKSEPWTLAL ENVVGAKNMN VRPLLNYFEP LFTWLKDQNK    600
NSFVGWSTDW SPYADQSIKV RISLKSALGD KAYEWNDNEM YLFRSSVAYA MRQYFLKVKN    660
QMILFGEEDV RVANLKPRIS FNFFVTAPKN VSDIIPRTEV EKAIRMSRSR INDAFRLNDN    720
SLEFLGIQPT LGPPNQPPVS IWLIVFGVVM GVIVVGIVIL IFTGIRDRKK KNKARSGENP    780
YASIDISKGE NNPGFQNTDD VQTSF                                          805

SEQ ID NO: 16           moltype = AA  length = 304
FEATURE                 Location/Qualifiers
source                  1..304
                        mol_type = protein
                        organism = SARSCoV2 virus
```

-continued

```
SEQUENCE: 16
VFNATRFASV YAWNRKRISN CVADYSVLYN SASFSTFKCY GVSPTKLNDL CFTNVYADSF  60
VIRGDEVRQI APGQTGKIAD YNYKLPDDFT GCVIAWNSNN LDSKVGGNYN YLYRLFRKSN  120
LKPFERDIST EIYQAGSTPC NGVEGFNCYF PLQSYGFQPT NGVGYQPYRV VVLSFELLHA  180
PATVCGPKKS TNLVKNKCVN FNFNGLTGTG VLTESNKKFL PFQQFGRDIA DTTDAVRDPQ  240
TLEILDITPC SFGGVSVITP GTNTSNQVAV LYQDVNCTEV PVAIHADQLT PTWRVYSTGS  300
NVFQ                                                               304

SEQ ID NO: 17          moltype = AA  length = 11
FEATURE                Location/Qualifiers
REGION                 1..11
                       note = linker
source                 1..11
                       mol_type = protein
                       organism = synthetic construct
SEQUENCE: 17
GGSGGGSGGG S                                                       11

SEQ ID NO: 18          moltype = AA  length = 6
FEATURE                Location/Qualifiers
REGION                 1..6
                       note = Histidine tag
source                 1..6
                       mol_type = protein
                       organism = synthetic construct
SEQUENCE: 18
HHHHHH                                                             6

SEQ ID NO: 19          moltype = AA  length = 321
FEATURE                Location/Qualifiers
REGION                 1..321
                       note = SARSCoV2 S protein RBD with linker and histidine tag
source                 1..321
                       mol_type = protein
                       organism = synthetic construct
SEQUENCE: 19
VFNATRFASV YAWNRKRISN CVADYSVLYN SASFSTFKCY GVSPTKLNDL CFTNVYADSF  60
VIRGDEVRQI APGQTGKIAD YNYKLPDDFT GCVIAWNSNN LDSKVGGNYN YLYRLFRKSN  120
LKPFERDIST EIYQAGSTPC NGVEGFNCYF PLQSYGFQPT NGVGYQPYRV VVLSFELLHA  180
PATVCGPKKS TNLVKNKCVN FNFNGLTGTG VLTESNKKFL PFQQFGRDIA DTTDAVRDPQ  240
TLEILDITPC SFGGVSVITP GTNTSNQVAV LYQDVNCTEV PVAIHADQLT PTWRVYSTGS  300
NVFQGGSGGG SGGGSHHHHH H                                            321
```